(12) United States Patent
Bäck et al.

(10) Patent No.: US 12,734,077 B2
(45) Date of Patent: Sep. 15, 2026

(54) DISPOSABLE PANT-TYPE ARTICLE HAVING CONTOURED LEG EDGES AND A METHOD FOR PRODUCING THE DISPOSABLE PANT-TYPE ARTICLE

(71) Applicant: Essity Hygiene and Health Aktiebolag, Gothenburg (SE)

(72) Inventors: Lucas Bäck, Gothenburg (SE); Fanny Stenholm, Gothenburg (SE); Helena Wallin, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 421 days.

(21) Appl. No.: 18/560,693

(22) PCT Filed: Jun. 9, 2021

(86) PCT No.: PCT/EP2021/065373
§ 371 (c)(1),
(2) Date: Nov. 14, 2023

(87) PCT Pub. No.: WO2022/258157
PCT Pub. Date: Dec. 15, 2022

(65) Prior Publication Data

US 2024/0252368 A1 Aug. 1, 2024

(51) Int. Cl.
*A61F 13/496* (2006.01)
*A61F 13/49* (2006.01)

(52) U.S. Cl.
CPC .... *A61F 13/4963* (2013.01); *A61F 13/49012* (2013.01); *A61F 13/49017* (2013.01)

(58) Field of Classification Search
CPC ............ A61F 13/4963; A61F 13/49012; A61F 13/49017; A61F 13/496; A61F 2013/49082; A61F 13/4906
See application file for complete search history.

(56) References Cited

U.S. PATENT DOCUMENTS 4,743,241 A * 5/1988 Igaue .................. A61F 13/4963
604/385.26
5,032,120 A 7/1991 Freeland et al.
(Continued)

FOREIGN PATENT DOCUMENTS

CO 2017011872 A2 2/2018
EP 1603502 B1 4/2016
(Continued)

OTHER PUBLICATIONS

International Search Report (PCT/ISA/210) and Written Opinion (PCT/ISA/237) mailed on Mar. 30, 2022 by the European Patent Office as the International Searching Authority for International Application No. PCT/EP2021/065373. (11 pages).
(Continued)

*Primary Examiner* — Rebecca E Eisenberg
*Assistant Examiner* — Gabriella E Burnette
(74) *Attorney, Agent, or Firm* — BUCHANAN INGERSOLL & ROONEY PC

(57) ABSTRACT

A disposable pant-type article including a front body panel and a rear body panel, each being elastically stretchable in a transverse direction, and a crotch region being located between a front panel crotch edge and a rear panel crotch edge. The article has first and second leg edges, each leg edge constituted by a front leg edge section, a rear leg edge section, and a crotch leg edge section. Each front leg edge section has an inner point located at a greater distance from a side seam than from a longitudinally extending centre line, the inner point being closer to the front waist edge than an outer point on the front leg edge section. Each crotch leg edge section has an intermediate point located between the front and rear crotch edges which is closer to the longitudinal centre line than a front endpoint of the crotch leg edge section.

22 Claims, 14 Drawing Sheets

(56) References Cited

U.S. PATENT DOCUMENTS

| | | | | |
|---|---|---|---|---|
| 5,445,628 | A | 8/1995 | Gipson et al. | |
| 6,213,991 | B1 | 4/2001 | Kling et al. | |
| 10,925,779 | B2 | 2/2021 | Matsumiya et al. | |
| 2001/0007935 | A1 | 7/2001 | Gompel et al. | |
| 2002/0151864 | A1 | 10/2002 | Otsubo et al. | |
| 2005/0010188 | A1 | 1/2005 | Glaug et al. | |
| 2008/0083489 | A1 | 4/2008 | Schneider et al. | |
| 2010/0168705 | A1* | 7/2010 | Stabelfeldt | A61F 13/4902 604/385.29 |
| 2011/0144611 | A1 | 6/2011 | Saito | |
| 2013/0211363 | A1 | 8/2013 | Lavon et al. | |
| 2013/0289513 | A1 | 10/2013 | Takino | |
| 2015/0065973 | A1 | 3/2015 | Roe et al. | |
| 2017/0216105 | A1 | 8/2017 | Bäck et al. | |
| 2018/0147098 | A1 | 5/2018 | Lindström | |
| 2019/0328586 | A1* | 10/2019 | Mukai | A61F 13/496 |

FOREIGN PATENT DOCUMENTS

| | | | |
|---|---|---|---|
| JP | H09506004 | A | 6/1997 |
| JP | 2006519938 | A | 8/2006 |
| JP | 2012143305 | A | 8/2012 |
| JP | 2017176658 | A | 10/2017 |
| JP | 2018526149 | A | 9/2018 |
| WO | 9506451 | A1 | 3/1995 |
| WO | 2004078082 | A1 | 9/2004 |
| WO | 2004078084 | A1 | 9/2004 |
| WO | 2011081578 | A1 | 7/2011 |
| WO | 2017044013 | A1 | 3/2017 |
| WO | 2017044014 | A1 | 3/2017 |

OTHER PUBLICATIONS

English translation of the Brazilian Office Action issued on Dec. 24, 2025, by the Brazilian Patent Office in corresponding Brazilian Patent Application No. BR112023024769-1. (4 pages).

Office Action issued on Dec. 2, 2025, by the Colombian Patent Office in corresponding Colombian Patent Application No. NC2023/0016800 with comment. (11 pages).

Office Action (Notice of Reasons for Rejection) issued on Sep. 30, 2024, by the Japanese Patent Office in corresponding Japanese Patent Application No. 2023-575925, and an English Translation of the Office Action. (13 pages).

* cited by examiner

130
MD
CD 121
119
103
118
122
110
120
131c
108
101
102
109
111
$L_d$
$L_d$
$L_p$
104
115
131b
131a

MD
CD
130
119
118
110
120
Ld
131c
108
101
103
102
163
162
142
109
160
111
Lc
Lp
104
161
141
131b
131a
151
150

DISPOSABLE PANT-TYPE ARTICLE HAVING CONTOURED LEG EDGES AND A METHOD FOR PRODUCING THE DISPOSABLE PANT-TYPE ARTICLE

TECHNICAL FIELD

The present disclosure pertains to a disposable pant-type article having a front body panel and a rear body panel, the body panels being elastically stretchable in a transverse direction of the article, the front body panel having a front panel waist edge, a front panel crotch edge opposite the front panel waist edge and a first and a second front panel side edge and the rear body panel having a rear panel waist edge, a rear panel crotch edge opposite the rear panel waist edge and a first and a second rear panel side edge. The article has a crotch region comprising a crotch region web, the crotch region being located between the front panel crotch edge and the rear panel crotch edge. The side edges of the front and rear body panels are joined in side seams to create a waist opening and first and second leg openings, the first leg opening having a first leg edge and the second leg opening having a second leg edge.

BACKGROUND

In the art of disposable pant-type articles and in particular disposable pant-type articles which are intended for use by adult users, the articles should meet high demands on fit, comfort and have a tailored and underwear like appearance while at the same time meeting equally high demands on absorbency and leakage protection. Disposable absorbent articles are articles which are intended to be discarded after a single use and not be laundered or otherwise restored for repeated use.

Pant-type articles of this kind are relatively complex products involving multiple components which are combined to form the absorbent article. Such components include nonwoven components, barrier components, elastic components and usually an absorbent core which may be provided in the form of an absorbent assembly including a barrier layer and a liquid permeable topsheet which together enclose the absorbent core. It is common to enhance body conformance and leakage security by arranging pre-tensioned elastic elements along all or selected parts of the waist opening and the leg openings of the pant-type article.

It has also been suggested in EP 1 603 502 B1 to improve body conformance of a pant-type article by providing the article with shaped leg edges. However, although the pant-type article in EP 1 603 502 B1 is well suited for some categories of users, the body build and body size differ greatly between users and there remains a need for well-fitting pant-type articles which may cater for the needs of a greater range of users.

However, there is an ongoing need for pant-type articles having good fit, and thereby good comfort and leakage security.

SUMMARY

Disposable pant-type articles having good functionality, fit and comfort, may be obtained by the features of claim 1. Disposable pant-type articles as set out herein may be produced according to the method of claim 15. Variations of the disclosure are set out in the dependent claims.

Disclosed herein is a disposable pant-type article, the article having a longitudinal direction and a transverse direction, with a longitudinal centre line extending in the longitudinal direction, the article comprising:

- a front body panel being elastically stretchable in the transverse direction, the front body panel having a front waist edge, a front crotch edge opposite the front waist edge and a first and a second longitudinal side edge;
- a rear body panel being elastically stretchable in the transverse direction, the rear body panel having a rear waist edge, a rear crotch edge opposite the rear waist edge and a first and a second longitudinal side edge;
- a crotch region being located between the front panel crotch edge and the rear panel crotch edge, the crotch region being contiguous with the front body panel along the front panel crotch edge and being contiguous with the rear body panel along the rear panel crotch edge.

The first longitudinal side edge of the front body panel is joined to the first longitudinal side edge of the rear body panel in a first side seam, and the second longitudinal side edge of the front body panel is joined to the second longitudinal side edge of the rear body panel in a second side seam. The article has a waist opening and a first and a second leg opening. The first leg opening is bordered by a first leg edge and the second leg opening is bordered by a second leg edge, each of the first and the second leg edges being constituted by a front leg edge section a crotch leg edge section and a rear leg edge section.

The front body panel comprises a front panel web being elastically stretchable in the transverse direction, the front leg edge section of each of the first and the second leg edge being arranged in the elastically stretchable front panel web.

The rear body panel comprises a rear panel web being elastically stretchable in the transverse direction, the rear leg edge section of each of the first and the second leg edge being arranged in the elastically stretchable rear panel web.

The crotch region comprises a crotch region web, the crotch leg edge section of each of the first and the second leg edge being arranged in the crotch region web from the front crotch edge of the front body panel to the rear crotch edge of the rear body panel.

Each front leg edge section has an inner point being located on the front leg edge section at a greater distance from the corresponding side seam than from the longitudinally extending centre line, and an outer point constituting an endpoint of the front leg edge section and being located at the corresponding side seam, a distance between the inner point of the front leg edge section and the front waist edge being the smallest distance between the front leg edge section and the front waist edge and being smaller than a distance between the outer point of the front leg edge section and the front waist edge.

Each crotch leg edge section has an intermediate point located between the front crotch edge and the rear crotch edge which intermediate point is closer to a longitudinal centre line than a front endpoint of the crotch leg edge section where the leg edge intersects with the front crotch edge.

The distance between the front endpoints of the crotch leg edge sections and the front waist edge may be greater than the distance between the outer points of the front leg edge sections and the front waist edge, such that the front endpoints of the crotch leg edge sections are placed lower than the outer points of the front leg edge sections.

The intermediate point on each crotch leg edge section may also be closer to the longitudinal centre line than a rear end point of the crotch leg edge section where the leg edge intersects with the rear crotch edge. Accordingly, the crotch region may have a smaller width at the intermediate points on the crotch leg edge section than at the front panel crotch edge and the rear panel crotch edge, giving the crotch region an hour-glass shape.

The distance between the outer point of each front leg edge section and the front waist edge may constitute the greatest distance between the front leg edge section and the front waist edge in a part of the front leg edge section which is defined between the inner point of the front leg edge section and the side seam.

The first leg edge and the second leg edge may be mirror symmetric about the longitudinally extending centre line.

The shape of the leg edges, with a higher cut close to the longitudinal centre line than at the side seams has been found to result in a more discreet and undergarment-like pant-type article in which the elasticity in the elastic front panel web has been fully utilized to obtain enhanced body conformance and comfort.

A distance between each inner point on each front leg edge section and the longitudinally extending centre line may be 30 to 50% of a distance between the longitudinally extending centre line and the corresponding side seam. The distances are measured in the transverse direction of the pant-type article, perpendicular to the longitudinally extending centre line.

During production of the pant-type articles as disclosed herein, the elastic materials, such as elastic elements, films and web materials are attached to non-elastic, non-stretchable materials with the elastic materials in a tensioned, stretched-out state. In the final pant-type articles, the elastic is relaxed, causing the non-stretchable materials to gather. The non-stretchable materials in a pant-type article as disclosed herein, limit the stretchability of elasticated parts of the pant-type article such as elastic front and rear panels, leg elastic, waist elastic, etc. All distances and lengths as disclosed herein are measured with the pant-type article in a flattened generally two-dimensional state with all elastic in the article stretched out to the full extent permitted by the non-stretchable components in the article and with all non-stretchable components in the article in a non-gathered state.

The distance between a point on the front and rear leg edge sections and the corresponding side seam is measured along the corresponding leg edge. The outer points of the front leg edge sections are the outer endpoints of the front leg edge sections and are located immediately inside the side seams without any distance between the outer point and the side seam.

The distance between the inner and outer points on the front leg edge sections and the corresponding waist edge is measured in the longitudinal direction. In embodiments wherein one or both waist edges are non-linear, such as wavy waist edges, the distance measured in the longitudinal direction y to a straight line extending in the transverse direction, parallel to and in the vicinity of the front waist edge.

The distance between the longitudinal centre line and each of the intermediate point and the front and rear end points on each crotch leg edge section is measured in the transverse direction.

The distance between the inner point on each front leg edge section and the front waist edge may be from 5 millimetres to 40 millimetres smaller, such as from 10 millimetres to 30 millimetres smaller, or from 15 millimetres to 20 millimetres smaller than the distance between the outer point on the front leg edge section and the front waist edge. Thus, the inner point on each front leg edge section may be arranged closer to the front waist edge than the outer point by at least 5 millimetres and by at most 40 millimetres, such as by at least 10 millimetres and by at most 30 millimetres, or by at least 15 millimetres and by at most 20 millimetres.

The inner point on each front leg edge section may be arranged closer to the front waist edge than the outer point by at most 20 millimetres.

In a pant-type absorbent article having an absorbent core, it has been found that particularly good body conformance and fit of the article, such as of an article of the "hipster" type, may be achieved if the inner points on the front crotch leg edge sections are located at or close to the side edges of the absorbent core.

The distance between the intermediate point on each crotch leg edge section and the longitudinal centre line may be smaller than the distance between the front endpoint and the longitudinal centre line by from 2 millimetres to 30 millimetres, such as from 5 millimetres to 20 millimetres or from 7 millimetres to 15 millimetres.

The distance between the intermediate point on each crotch leg edge section and the longitudinal centre line may be smaller than the distance between the rear endpoint and the longitudinal centre line by from 5 millimetres to 60 millimetres, such as from 10 millimetres to 50 millimetres, or from 12 millimetres to 40 millimetres, or from 15 millimetres to 30 millimetres smaller than the distance between the rear endpoint and the longitudinal centre line.

The crotch region may comprise a crotch panel which is attached with a first side edge of the crotch panel to the front body panel along the front panel crotch edge, and with a second side edge of the crotch panel attached to the rear body panel along the rear panel crotch edge. The attachments between the crotch panel and the front and rear panels may be made as overlap seams extending along the front panel crotch edge and the rear panel crotch edge.

Alternatively, or in addition thereto, the crotch region may comprise a portion of a web material, such as an inner or outer cover web material of the pant-type article which extends continuously in the longitudinal direction from the front panel waist edge to the rear panel waist edge and bridges a gap between the front panel crotch edge and the rear panel crotch edge. The portion of the continuous cover web material which is applied in the crotch region constitutes the crotch region web.

In either case, the longitudinal extension of the crotch region in the longitudinal direction is defined as the distance in the longitudinal direction between the front panel crotch edge of the elastically stretchable front body panel and the rear panel crotch edge of the elastically stretchable rear body panel. It may be preferred that the crotch region web extends over the entire surface of the crotch region.

The crotch region web, which is applied in the crotch region, either as part of a coherent cover material or as a crotch panel material may be a non-elastic material, such as a non-stretchable nonwoven web.

Each rear leg edge section of a disposable pant-type article as disclosed herein may have a convex curved buttocks portion.

Each rear leg edge section may have a transition point where the convex curvature of the buttocks portion of the rear leg edge section changes into a linear hip portion of the rear leg edge section or into a hip portion having a concave curvature, the transition point being located at a distance from the corresponding side seam, such as at a distance of from 30 millimetres to 100 millimetres from the corresponding side seam.

The shape of the leg edges of a pant-type article as disclosed herein may be described as each of the first leg edge and the second leg edge having a shape corresponding to half the contour of a heart-shaped area.

The pant-type article as disclosed herein may further comprise an absorbent core. The absorbent core may be part of an absorbent assembly, the absorbent assembly comprising an absorbent core, a liquid permeable topsheet and a liquid impermeable backsheet, the absorbent core being enclosed between the liquid permeable topsheet and the liquid impermeable backsheet.

The absorbent assembly has side edges extending in the longitudinal direction of the pant-type article and end edges extending the transverse direction of the pant-type article.

The absorbent assembly may further comprise leg elastic elements applied along the side edges of the absorbent assembly.

The intermediate point on each crotch leg edge section where the distance between the crotch leg edge section and the longitudinal centre line is smaller than the distance between the front endpoint and the longitudinal centre line and optionally smaller than distance between the rear endpoint of the crotch leg edge section and the longitudinal centre line, may be arranged on a side edge of the absorbent assembly.

A pre-tensioned first crotch elastic member may be arranged extending in the longitudinal direction along the first leg edge between the front crotch edge and the rear crotch edge and a pre-tensioned second crotch elastic member may be arranged extending in the longitudinal direction along the second leg edge between the front crotch edge and the rear crotch edge.

The intermediate point on each crotch leg edge section where the distance between the crotch leg edge section and the longitudinal centre line is smaller than the distance between the front endpoint and the longitudinal centre line and optionally smaller than distance between the rear endpoint of the crotch leg edge section and the longitudinal centre line, may be arranged on a side edge of the corresponding crotch elastic member.

In the disposable pant-type article as disclosed herein, the crotch elastic members each have a front end portion at the front panel crotch edge and a rear end portion at the rear panel crotch edge, wherein the front end portion of each of the first and the second crotch elastic members may overlap with and be attached to the front body panel and/or the rear end portion of each of the first and the second crotch elastic members may overlap with and be attached to the rear body panel.

The crotch elastic members may be flat, band-shaped crotch elastic members and may comprise or consist of elastic film.

The crotch elastic members may have a width in the transverse direction of the article in the range of from 15 mm to 50 mm, such as from 20 mm to 40 mm or from 25 mm to 35 mm, and a length in the longitudinal direction of the article in the range of from 150 mm to 350 mm, such as from 170 mm to 320 mm or from 200 mm to 310 mm. The dimensions of the crotch elastic members are measured with the pant-type article in a flat-out state with the side seams broken or cut open.

Each of the first crotch elastic member and the second crotch elastic member may have a greater width in the front and rear end portions of the crotch elastic member than in an intermediate portion of the crotch elastic member being arranged between the front end portion and the rear end portion of the crotch elastic member.

The width of the front end portion may be equal to the width of the rear end portion. A ratio between the width of the end portions and the smallest width of the intermediate portion may be from 1:0.5 to 1:0.9.

The concavely curved part of the crotch elastic member may have a radius of curvature of from 200 to 700 mm.

Pre-tensioning of the crotch elastic members may suitably be achieved by attaching the crotch elastic members to the pant-type article with the crotch elastic members being in a stretched state. The crotch elastic member may be applied and attached to the pant-type article with the end portions of the crotch elastic members in a non-tensioned condition. The non-tensioned end portions of the crotch elastic members may each have a length of from 5% to 8% of the total length of the crotch elastic member, including the length of the end portions and the tensioned intermediate portion between the end portions.

The absorbent assembly, if present, may be applied to cover the stretched and attached crotch elastic members. In this manner the absorbent assembly will be overlaying the crotch elastic members on the inner surface of the pant-type article, the inner surface being the surface which is intended to be facing the wearer when the pant-type article is being worn. The inner surface of the absorbent assembly may be formed by the liquid permeable topsheet and may optionally include reinforcing elastic elements and/or barrier cuffs extending along the side edges of the absorbent assembly.

It may be preferred that the topsheet of the absorbent assembly and any barrier cuffs are formed from fibrous web material, such as nonwoven material, providing the inner surface of the absorbent assembly with a textile character. Barrier cuffs may be elastic barrier cuffs.

A first reinforcing elastic feature may be arranged on the elastically stretchable rear body panel web along part or all of the rear leg edge section of the first leg edge and a second reinforcing elastic feature may be arranged on the elastically stretchable rear body panel web along part or all of the rear leg edge section of the second leg edge. The reinforcing elastic features are supplementary elastic elements which are applied in addition to the elastic material in the elastic body panels.

The first reinforcing elastic feature may extend along a first part of the rear leg edge section of the first leg edge in a direction away from the longitudinal centre line of the pant-type article towards the first side seam. The first reinforcing elastic feature may have an end point on the rear leg edge section of the first leg edge, with a second part of the rear leg edge section of the first leg edge being free from the first reinforcing elastic feature. The second part of the rear leg edge section of the first rear leg edge may have a length as measured along the first leg edge from the end point of the first reinforcing elastic feature to the first side seam which is from 25% to 75% of a total length of the rear leg edge section of the first leg edge.

The second reinforcing elastic feature may extend along a first part of the rear leg edge section of the second leg edge in a direction away from the longitudinal centre line of the pant-type article towards the second side seam. The second reinforcing elastic feature may have an end point on the rear leg edge section of the second leg edge, with a second part of the rear leg edge section of the second leg edge being free from the second reinforcing elastic feature. The second part of the rear leg edge section of the second leg edge may have a length as measured along the second leg edge from the end point of the second reinforcing elastic feature to the second side seam which is from 25% to 75% of a total length of the rear leg edge section of the second leg edge.

The first reinforcing elastic feature and the second reinforcing elastic feature of the pant-type article as disclosed herein may be formed from an elastic member which has been applied continuously between the side edges of the pant-type article and subsequently cut to provide elastification only along the parts of the rear leg edge sections where reinforced elastic is desired. The continuous elastic member may also have been cut at a location corresponding to the longitudinal centre line of the pant-type article and allowed to snap-back to attachment areas arranged at the intersections between the rear leg edge sections and the crotch leg edge sections, to avoid elastic contraction of the crotch area of the article.

The first and second reinforcing elastic features may comprise multiple individual elastic elements, such as 2 to 15 individual elastic elements, 3 to 12 individual elastic element or 4 to 10 individual elastic elements.

The multiple individual elastic elements may be elastic strings, threads or bands which are applied spaced apart along the rear leg edge sections of the first and second leg edges.

The reinforcing elastic features may be covered with a nonwoven covering web.

The reinforcing elastic features may intersect with and be attached to the first and the second crotch elastic members. The first and second crotch elastic members may have been attached in the crotch region before attaching the reinforcing elastic feature or the reinforcing elastic feature may have been attached in the crotch region before attaching the crotch elastic members. As set out herein, the rear end portion of the first crotch elastic member and the rear end portion of the second crotch elastic member may overlap with and be attached to the elastic rear body panel. The reinforcing elastic feature may then overlie and be attached to the rear end portion of the first crotch elastic member and to the rear end portion of the second crotch elastic member. The rear end portions of the crotch elastic members may, thus, serve as anchoring areas for the reinforcing elastic features at an inner end of the reinforcing elastic feature.

It may be advantageous that the reinforcing elastic feature is attached to non-tensioned end portions of the crotch elastic members as a more secure attachment between the reinforcing elastic element and the crotch elastic members may be provided in this manner.

In a disposable pant-type article as disclosed herein, the elastically stretchable front body panel web and/or the elastically stretchable rear body panel web may comprise or consist of an elastic laminate, the elastic laminate comprising first and second layers of fibrous material and an intermediate elastic layer arranged between the first and second layers of fibrous material.

The intermediate elastic layer may comprise or consists of a layer of elastic film.

It may be desirable that all sections of the first leg edge and the second leg edge are cut in an elastic web material, such that an elastic film, an elastic nonwoven or an elastic foam material, with a primary direction of the cut being in the direction of stretchability of the elastic material, i.e., the front and rear leg edge sections are cut primarily in the transverse direction and the crotch leg edge sections are cut primarily in the longitudinal direction and extend at least partially in crotch elastic members which are pre-tensioned in the longitudinal direction.

A part of each leg cut which extends in the crotch region web may be cut through the crotch region web, through a corresponding crotch elastic member, if present, and through a peripheral edge portion of an absorbent assembly, if present, the peripheral edge portion of the absorbent assembly being formed by one or both of the liquid impermeable backsheet and the liquid permeable topsheet of the absorbent assembly, the peripheral edge portion of the absorbent assembly being arranged outward of a peripheral edge of the absorbent core of the absorbent assembly. In an absorbent assembly as disclosed herein, the topsheet and the backsheet may both extend beyond the periphery of the absorbent core and may be joined to each other in an edge seal extending along the periphery of the absorbent core outward of a peripheral edge of the absorbent core.

A leg cut which is formed through a peripheral edge portion of an absorbent assembly and optionally through a crotch elastic member will have the intermediate point on the crotch leg edge section where the distance between the crotch leg edge section and the longitudinal centre line is smaller than the distance between the front endpoint and the longitudinal centre line and optionally also smaller than the distance between the rear endpoint of the crotch leg edge section and the longitudinal centre line, located on a side edge of the absorbent assembly and optionally also on a side edge of the crotch elastic member.

Each crotch elastic member has a concave edge resulting from the leg cut through the layers of material in the crotch region having been made along a concave line. A concave edge, as referred to herein may be a continuously curved concave edge or may be an edge comprising two or more straight segments and optionally one or more curved segments. A concave edge, as referred to herein includes V-shapes and U-shapes as well as any other shape providing the pant-type absorbent article with crotch region which is narrower in a longitudinally intermediate part of the crotch region than at the end parts of the crotch region. A concave edge of a crotch elastic member which has been formed by simultaneous cutting through multiple layers of material in the crotch region, including one or more layers from a peripheral edge portion of an absorbent assembly, is coincident with a concave edge of the liquid permeable topsheet and/or with a concave edge of the liquid impermeable backsheet of the absorbent assembly.

The liquid impermeable backsheet and/or the liquid permeable topsheet of the absorbent assembly may, thus, be coterminous with the first and the second crotch elastic members along at least a part of the concave crotch leg edge sections which extend in the crotch elastic members, such as along a part of each concave crotch leg edge section which is arranged in an intermediate portion of the corresponding crotch elastic member.

A pant-type absorbent article having concave crotch leg edge sections in which the leg edge shape of a crotch elastic member has been created by the crotch elastic member being cut together with the crotch region web and preferably one or more additional web materials, such as a topsheet and/or a backsheet of an absorbent assembly provides the pant-type absorbent article with cuff-like, non-wrinkled elastic leg edges which conforms comfortably to the groin of a wearer.

In a disposable pant-type article as disclosed herein, the elastically stretchable front body panel web may form part of or constitute a continuous front panel web which extends transversely between the first and the second front panel side edges and which extends longitudinally from the front waist edge to the front crotch edge and/or wherein the elastically stretchable rear body panel forms part of or constitutes a continuous rear panel web which extends transversely across the width of the rear portion between the first and the second rear panel side edges and which extends longitudinally from the rear waist edge to the rear crotch edge.

Disclosed herein is also a continuous method of producing disposable pant-type articles, such as the disposable pant-type articles disclosed herein, the method comprising the steps of:

advancing a continuous elastically stretchable front panel web in a machine direction, the front panel web being tensioned in the machine direction and having a front waist edge and an opposing front crotch edge;

advancing a continuous elastically stretchable rear panel web in a machine direction, the rear panel web being tensioned in the machine direction and having a rear waist edge and an opposing rear crotch edge, the rear panel web being spaced apart from the front panel web in a cross machine direction, perpendicular to the machine direction with a gap in the cross machine direction between the crotch edge of the front panel web and the crotch edge of the rear panel web;

advancing a non-elastic continuous crotch web in the machine direction, the crotch web having a first side edge and an opposing second side edge;

attaching the crotch web to the tensioned front panel web and to the tensioned rear panel web, thereby bridging the gap between the front crotch edge of the front panel web and the rear crotch edge of the rear panel web and forming a continuous chassis web of interconnected precursor articles, the precursor articles being connected at dividing lines extending in the cross machine direction between the precursor articles;

forming leg cuts in the chassis web, each leg cut having a closed loop configuration and forming a first leg edge of a leading precursor article and a second leg edge of a trailing precursor article, the first leg edge of the leading precursor article having a front leg edge section cut in the front panel web, a crotch leg edge section cut in the crotch web from the front crotch edge of the front panel web to the rear crotch edge of the rear panel web and a rear leg edge section cut in the rear panel web, the second leg edge of the trailing precursor article having a front leg edge section cut in the front panel web, a crotch leg edge section cut in the crotch web and a rear leg edge section cut in the rear panel web, wherein each front leg edge section has an inner point being located on the front leg edge section at a greater distance from the corresponding side seam than from the longitudinally extending centre line, and an outer point being located on the front leg edge section at the corresponding side seam, a distance between the inner point of the front leg edge section and the front waist edge being the smallest distance between the front leg edge section and the front waist edge and being smaller than a distance between the outer point of the front leg edge section and the front waist edge, each crotch leg edge section has a point located between the front crotch edge and the rear crotch edge, where the distance between the first leg edge and the second leg edge is smaller than at the endpoint of the crotch leg edge section where the leg edge intersects with the front crotch edge;

folding the chassis web along a fold-line extending in the machine direction and bringing the waist edge of the front panel web into alignment with the waist edge of the rear panel web;

forming first and second side seams in each precursor article, the side seams being formed in the cross machine direction from the aligned waist edges of the front and rear panel webs to the leg cuts; and severing individual pant-type articles from the chassis web.

The elastically stretchable front panel web and/or the elastically stretchable rear panel web comprises or consists of an elastic laminate, the elastic laminate comprising at least a first layer of non-stretchable fibrous material, such as a nonwoven web, and an elastic layer.

The elastic laminate may comprise a second layer of fibrous material and the elastic layer may be an intermediate elastic layer arranged between the first and the second layer of fibrous material.

The elastic layer in a laminate as disclosed herein may comprise or consists of a layer of elastic film.

The elastic layer in a laminate as disclosed herein may comprise or consists of a layer of elastic nonwoven material.

One or both of the front panel web and the rear panel web may comprise or consists of a tri-laminate web comprising two outer nonwoven layers and an intermediate elastic layer between the outer nonwoven layers. A three-layer nonwoven-film-nonwoven laminate provides elastic panels with smooth, soft and skin-friendly textile-like surfaces. The laminate may be produced by any known method or combination of methods such as stretch-bonding methods, methods involving incremental stretching, etc.

A three-layer elastic panel web may be formed by stretch-bonding a first surface of an elastic layer, such as an elastic film, an elastic nonwoven or by stretch-bonding multiple parallel elastic elements such as strings or filaments to a first nonwoven layer and subsequently bonding a second nonwoven layer to a second surface of the elastic layer or to cover the multiple parallel elastic strings on the first nonwoven layer. Stretch bonding implies that the elastic layer or the elastic elements are stretched, such as by 50-600% in the machine direction MD, to retain the elastic properties of the elastic film layer in the compound base web.

When using laminate elastic panel webs comprising a stretch-bonded elastic layer or elastic elements and one or more non-stretchable layers, such as one or more non-stretchable nonwoven layers in the method as disclosed herein, the webs are held tensioned, throughout the process up until the final step of severing individual pant-type articles from the chassis web. This generally means that the webs are stretched in the machine direction to the maximum extent permitted by the non-stretchable layer or layers.

The crotch web as disclosed herein may be any suitable non-stretchable web material, such as a non-stretchable nonwoven web, a non-stretchable polymer film or a non-stretchable laminate. Laminates comprising one or more nonwoven webs and laminates comprising one or more nonwoven webs and a polymer film are also conceivable. The crotch web may be a crotch panel web having a first side edge and an opposing second side edge, the first side edge of the crotch panel web being attached in a front seam to the front crotch edge of the tensioned front panel web and the second side edge of the crotch panel web being attached in a rear seam to the rear crotch edge of the tensioned rear panel web, thereby bridging the gap between the front crotch edge of the front panel web and the rear crotch edge of the rear panel web. Alternatively, the crotch web may be an outer or inner cover web extending in the cross machine direction the full distance or at least 75% of the distance between the front waist edge and the rear waist edge.

The method as disclosed herein may further comprise:

providing a pair of crotch elastic members, consisting of a first pre-fabricated crotch elastic member and a second pre-fabricated crotch elastic member;

stretching each crotch elastic member in a longitudinal direction of the crotch elastic member and aligning the longitudinal direction of the crotch elastic member with the cross machine direction;

attaching each stretched crotch elastic member to the crotch panel web while keeping the crotch elastic member stretched and aligned with the cross machine direction, the first crotch elastic member being spaced apart from the second crotch elastic member with a crotch spacing in the machine direction, a pair of crotch elastic members of a leading precursor article being spaced apart from a pair of crotch elastic members of a trailing precursor article with an article spacing in the machine direction, the article spacing being dependent on a pitch-length of the precursor articles in the chassis web of interconnected precursor articles.

In the method as disclosed herein, the crotch elastic members may be band-shaped crotch elastic members. The band-shaped crotch elastic members may be strips of inherently elastic material such as elastic film or elastic nonwoven material or may be pre-fabricated elastic members comprising one or more layers of non-elastic webs to which one or more elastic elements have been bonded in a tensioned state. Such elastic elements may be multiple elastic strings, threads or bands which are applied parallel to each other in the length direction of the crotch elastic member corresponding to the cross machine direction of the method and which are spaced-apart in the width direction of the crotch elastic member, corresponding to the machine direction of the method. Laminates of elastic film and one or more non-elastic nonwoven webs are also contemplated for the crotch elastic members as disclosed herein.

In the method as disclosed herein, it may be preferred that the crotch elastic members comprise or consist of elastic film.

The stretched crotch elastic members may have a width as measured in the machine direction in the range of from 15 mm to 50 mm, such as from 20 mm to 40 mm or from 25 mm to 35 mm, and a length as measured in the cross machine direction in the range of from 150 mm to 350 mm, such as from 170 mm to 320 mm or from 200 mm to 310 mm.

The method as disclosed herein may comprise overlapping a first end portion of each of the first and the second crotch elastic member of the pair of crotch elastic members with the tensioned front panel web and attaching the overlapping first end portion of each of the first and the second crotch elastic member to the tensioned front panel web and/or overlapping a second end portion of each of the first and the second crotch elastic member of the pair of crotch elastic members with the tensioned rear panel web and attaching the overlapping second end portion of each of the first and the second crotch elastic member to the tensioned rear panel web.

When stretching and applying the stretched crotch elastic members to the chassis web, the end portions of the crotch elastic members may be held in movable clamps in a stretching device. The clamped end portions are not subjected to stretching and will be applied and attached to the chassis web in a non-tensioned condition. The two non-tensioned end portions of each crotch elastic member may have a combined extension in the cross machine direction (i.e. in the length direction of the crotch elastic members) of from 10% to 15% of the total extension of the stretched crotch elastic member in the cross machine direction.

In a method as disclosed herein, and including applying tensioned crotch elastic members, the front sections of the leg edges may be formed by cutting mainly in the direction of tensioning of the front panel web and the crotch sections of the leg edges are formed by cutting mainly in the direction of tensioning of the first and the second crotch elastic member.

The method as disclosed herein may further comprise applying and attaching a pre-fabricated absorbent assembly between the first and second leg edges of each precursor article, the absorbent assembly comprising an absorbent core, the absorbent core being arranged between a liquid impermeable backsheet and a liquid permeable topsheet.

The absorbent assembly has side edges extending in a longitudinal direction of the absorbent assembly corresponding to the cross machine direction of the method and end edges extending in a cross direction of the absorbent assembly, corresponding to the machine direction of the method. The absorbent assembly may further comprise leg elastic elements applied along the side edges of the absorbent assembly.

The absorbent assembly may be applied to cover stretched and attached crotch elastic members. In this manner the absorbent assembly will be overlaying the crotch elastic members on the inner surface of the pant-type article which is being produced, the inner surface being the surface which is intended to be facing the wearer when the pant-type article is being worn. An inner surface of the absorbent assembly may be formed by the liquid permeable topsheet and may optionally include barrier cuffs extending along the side edges of the absorbent assembly.

It may be preferred that the topsheet of the absorbent assembly and any barrier cuffs are formed from fibrous web material, such as nonwoven material, providing the inner surface of the absorbent assembly with a textile character.

An absorbent core in a pant-type article as disclosed herein is not necessarily part of a pre-fabricated absorbent assembly comprising a topsheet and a backsheet.

The method as disclosed herein may also comprise attaching a waist elastic member along the front waist edge of the front panel web and/or attaching a waist elastic member along the rear waist edge of the rear panel web, the waist elastic member or waist elastic members being attached before or after attaching the crotch panel web to the front panel web and the rear panel web. The waist elastic member or waist elastic members may be attached to the waist edge of one or both of the front panel web and the rear panel web before the front panel web and the rear panel web are attached to the crotch panel web.

The waist elastic member may be attached to the front panel web and the rear panel web in accordance with a method as disclosed in WO 2017/044013 A1 or WO 2017/044014 A1 involving attaching a continuous waistband component to a base web in a defined waistband attachment area and severing the base web and the attached waistband component along a cutting line extending through the attachment area in the machine direction thereby creating a first panel web comprising a first panel portion with a first portion of the waistband component attached thereto and a second panel web comprising a second panel portion and a second portion of the waistband component attached thereto. After severing the base web and the elastic waistband component, the two web parts are shifted in the cross machine direction such that the edges of the web parts along which the parts of the waistband component are attached are facing away from each other instead of facing towards each other. The two web parts with the attached parts of the waistband component may be used in the method of producing disposable pant-type articles as disclosed herein as a front panel web having a waist elastic member arranged along the waist edge of the front panel web and a rear panel web having a waist elastic member arranged along the waist edge of the rear panel web.

Alternatively, the waist elastic member may be attached to the waist edge of one or both of the front panel web and the rear panel web after attaching the front panel web and the rear panel web to the crotch panel web.

The waistband member is a component of the chassis web which is configured for creating a well-defined waistband in a final pant-type article as disclosed herein. Each waistband member has an outer edge facing away from the crotch edge of the corresponding panel web and an inner edge facing towards the crotch edge of the corresponding panel web. The inner edge of the waistband member constitutes a well-defined boundary between the waistband member and a body-portion of the corresponding panel web.

Depending on how the waistband member is applied to the panel web, the waistband member may be completely overlapping with a waist edge part of the panel web, as in the application method disclosed in WO 2017/044013 A1 and WO 2017/044014 A1 or the waistband member may be attached to the waist edge of the panel web with only a small overlap, sufficient to create a join between the waistband member and the panel web.

The method as disclosed herein may involve feeding and stretching a continuous reinforcing leg elastic member in the machine direction and attaching the reinforcing leg elastic member in a stretched state in a curved configuration along the rear panel crotch edge before forming the leg cuts in the chassis web.

The continuous reinforcing leg elastic member is stretched in the machine direction and is attached in the stretched state along the crotch edge of the tensioned rear panel web before forming the leg cuts in the chassis web. Thereby, surplus parts of the elastic element may be cut away when forming the leg cut-outs.

The continuous leg elastic member may comprise multiple individual elastic elements, such as 2 to 15 elastic elements, 3 to 12 elastic element or 4 to 10 elastic elements.

The multiple individual elastic elements may be elastic strings, threads or bands which are applied spaced apart in the cross machine direction.

Attaching the continuous reinforcing elastic element may comprise forming an attachment area or multiple attachment areas on the tensioned rear panel web by applying adhesive to the tensioned rear panel web; attaching the continuous reinforcing elastic element to the tensioned rear panel web in the attachment area or attachment areas. The adhesive and the reinforcing elastic member which is applied to the adhesive may be covered by a covering web, such as a nonwoven covering web.

If present, the first and second crotch elastic members may be attached to the chassis web before attaching the reinforcing elastic element. In embodiments where the second end portions of the first and second crotch elastic members overlaps with and are attached to the tensioned rear panel web, and further are attached to the reinforcing elastic element, it may be preferred that the reinforcing elastic element overlies and is attached to the second end portion of the first and second crotch elastic members.

It may be advantageous that the reinforcing elastic element is attached to non-tensioned end portions of the crotch elastic members as a more reliable attachment between the reinforcing elastic element and the crotch elastic members may be obtained in this manner.

A part of each leg cut which extends in the crotch panel web may be cut through the crotch panel web, through a corresponding crotch elastic member and through a peripheral edge portion of an absorbent assembly, the peripheral edge portion of the absorbent assembly being formed by one or both of the liquid impermeable backsheet and the liquid permeable topsheet of the absorbent assembly, the peripheral edge portion of the absorbent assembly being arranged outward of a side edge of the absorbent core of the absorbent assembly. In an absorbent assembly as disclosed herein, the topsheet and the backsheet may both extend beyond the periphery of the absorbent core and may be joined to each other in an edge seal extending along the periphery of the absorbent core outward of a peripheral edge of the absorbent core.

In the method as disclosed herein, the first leg edge of each precursor article in the chassis web may consists of:

a front leg edge section extending in the tensioned front panel web, with a main direction of extension of the front leg edge section being in the machine direction;
a crotch leg edge section extending in the crotch panel web between the front panel crotch edge and the rear panel crotch edge, with a main direction of extension of the crotch leg edge section being in the cross machine direction; and
a rear leg edge section extending in the tensioned rear panel web, with a main direction of extension of the rear leg edge section being in the machine direction; and the second leg edge of each precursor article consists of:

a front leg edge section extending in the tensioned front panel web, with a main direction of extension of the front leg edge section being in the machine direction;
a crotch leg edge section extending in the crotch panel web between the front panel crotch edge and the rear panel crotch edge, with a main direction of extension of the crotch leg edge section being in the cross machine direction; and
a rear leg edge section extending in the tensioned rear panel web, with a main direction of extension of the rear leg edge section being in the machine direction.

After application of a reinforcing elastic element on the tensioned rear panel web, the method as disclosed herein may comprise forming the rear leg edge section of the first and second leg edges and simultaneously cutting away surplus parts of the reinforcing elastic element, leaving a remaining part of the reinforcing elastic element being attached along the rear leg edge section of each of the first leg edge and the second leg edge between a rearward point of each leg edge where the leg edge intersects with the rear panel crotch edge and a cutting point on the leg edge where the reinforcing elastic element is cut off.

Thus, a portion of each rear leg edge section between the cutting point and the dividing line between adjacent precursor articles which is closest to the cutting point, is free from reinforcing elastic. The portion of each rear leg edge section which is free from the reinforcing elastic element may have a length as measured along the corresponding leg edge from the cutting point to the closest dividing line which is from 25% to 75% of the total length of the rear leg edge section.

BRIEF DESCRIPTION OF THE DRAWINGS

The pant-type articles and the method for their production as disclosed herein will be further explained hereinafter with reference to the appended drawings wherein.

DETAILED DESCRIPTION

It is to be understood that the drawings are schematic and that individual components or features, such as layers of material are not necessarily drawn to scale. The absorbent pant-type incontinence article for adult users which is shown in the figures is provided as an example only. By an "absorbent pant-type article" as used herein is implied a pant-type article that absorbs or is adapted to absorb bodily fluids, such as urine, blood and loose fecal matter.

Pant-type articles without an absorbent core or with an absorbent core which is not part of an absorbent assembly are also conceivable, as disclosed herein. Furthermore, the absorbent pant-type article may be a baby diaper, a training pant, a feminine hygiene pant, swimwear, disposable underpants, etc.

The pant-type article which is shown in the figures is a simplified article, and the article may contain further features, such as barrier cuffs, disposal means, etc. It is also to be understood that the waist elastic disclosed herein is optional or that any other suitable type of waist elastic may be used. The side seams may be reclosable side seams, and the pant-type article may be provided with fastener elements to provide reclosability of the side seams.

The method for producing a pant-type article as disclosed herein is described herein in the context of a disposable pant-type article comprising an absorbent assembly. However, it is to be understood that the method is equally applicable to the production of absorbent and non-absorbent pant-type articles which do not comprise an absorbent assembly. The method as disclosed herein is useful in the production of any type of disposable pant-type article, such as adult incontinence articles, baby diapers, training pants, swim-pants, disposable underpants, sanitary pants for feminine use, etc.

Figure 1A:
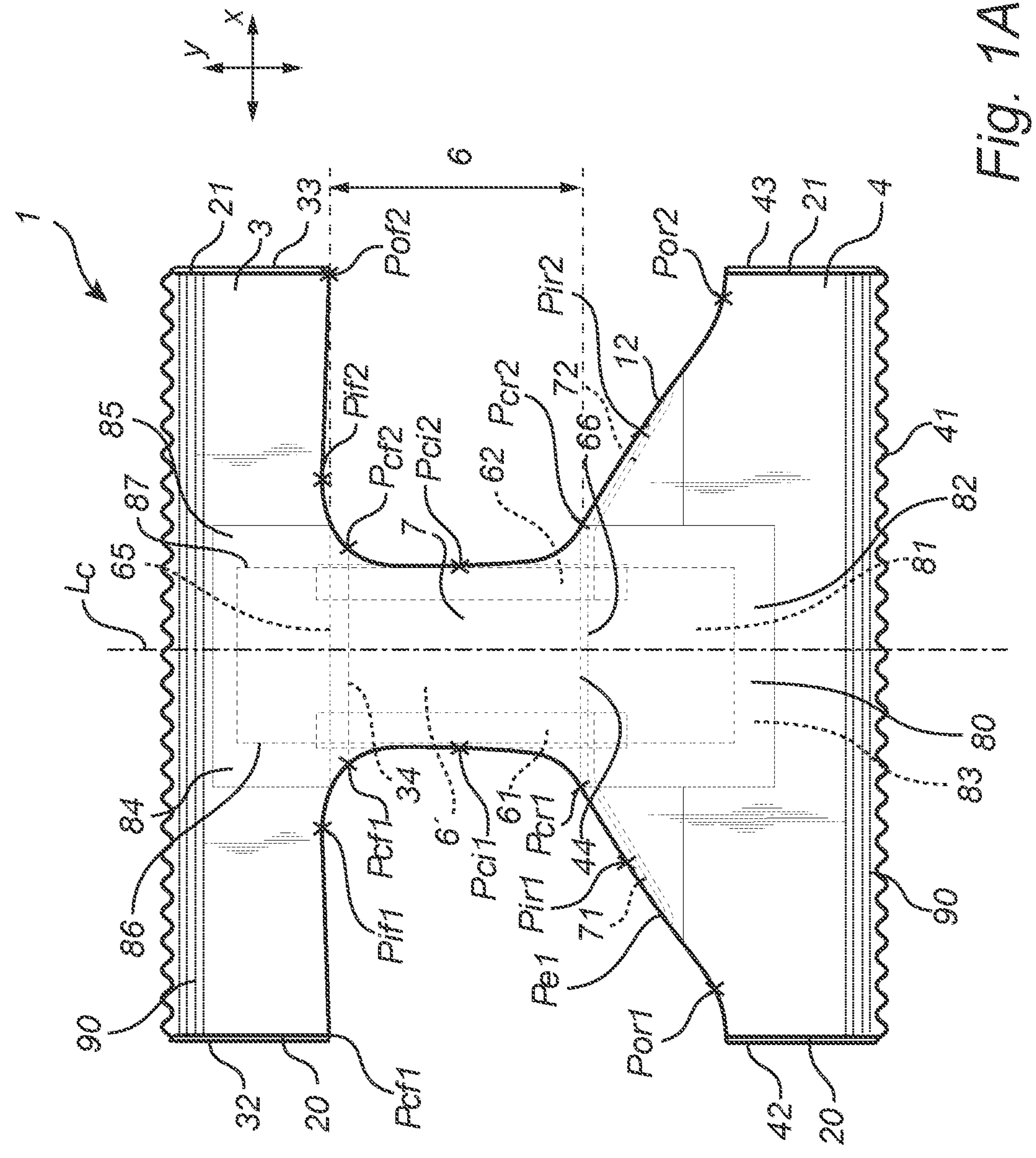
FIG. 1A shows a planar view of a stretched-out absorbent pant-type article with open side seams, as seen from an inner surface of the pant-type article.

With initial reference to FIG. 1A, there is shown a pant-type article 1 in the form of a pant-type incontinence article for adult users. The pant-type article 1 is shown in FIG. 1A in an unfolded and flat condition with all elastic elements in an extended state. The pant-type article has a longitudinal direction y and a transverse direction x. As set out herein, all measurements of distances and dimensions are made with the pant-type article in the fully stretched-out, non-gathered condition as shown in FIGS. 1A, 1B, 3 and 4.

The pant-type article 1 is seen from the inner surface which is the surface which will be facing a wearer's body when the article is being worn and which is opposite the outer, garment-facing surface of the pant-type article 1.

The pant-type article 1 comprises a front body panel 3, a rear body panel 4 and an absorbent assembly 80 located in a crotch region 6 of the pant-type article 1 and extending in the longitudinal direction y forward in over the front body panel 3 and rearward in over the rear body panel 4. The absorbent assembly 80 bridges a gap between the front and rear body panels 3, 4. The absorbent assembly 80 is a separately produced component which comprises an absorbent core 81, which is enclosed between a liquid permeable topsheet 82 and a liquid impermeable backsheet 83.

The front body panel 3 has a front panel waist edge 31 extending in the transverse direction x, a pair of front panel side edges 32, 33 extending in the longitudinal direction y and a front panel crotch edge 34 extending in the transverse direction opposite the front panel waist edge 31. The rear body panel 4 has a rear panel waist edge 41 extending in the transverse direction x, a pair of rear panel side edges 42, 43 extending in the longitudinal direction y and a rear panel crotch edge 44 extending in the transverse direction x opposite the rear panel waist edge 41.

In the pant-type article 1 shown in the figures, the elastically stretchable front body panel 3 has been formed from a continuous front body panel which extends in the transverse direction x across the width of the pant-type article 1 between the first and the second front panel side edges 32, 33 and which extends in the longitudinal direction from the front waist edge 31 to the front crotch edge 34. The elastically stretchable rear body panel 4 has been formed from a continuous rear body panel web which extends in the transverse direction x across the width of the pant-type article 1 between the first and the second rear panel side edges 42, 43 and which extends in the longitudinal direction y from the rear waist edge 41 to the rear crotch edge 34.

The crotch region 6 is arranged between the front body panel 3 and the rear body panel 3 and is contiguous with the front body panel 3 along the front panel crotch edge 34 and is contiguous with the rear body panel 4 along the rear panel crotch edge 44. The extension of the crotch region 6 in the longitudinal direction y is defined as the distance in the longitudinal direction between the front panel crotch edge 34 and the rear panel crotch edge 44.

Figure 4:
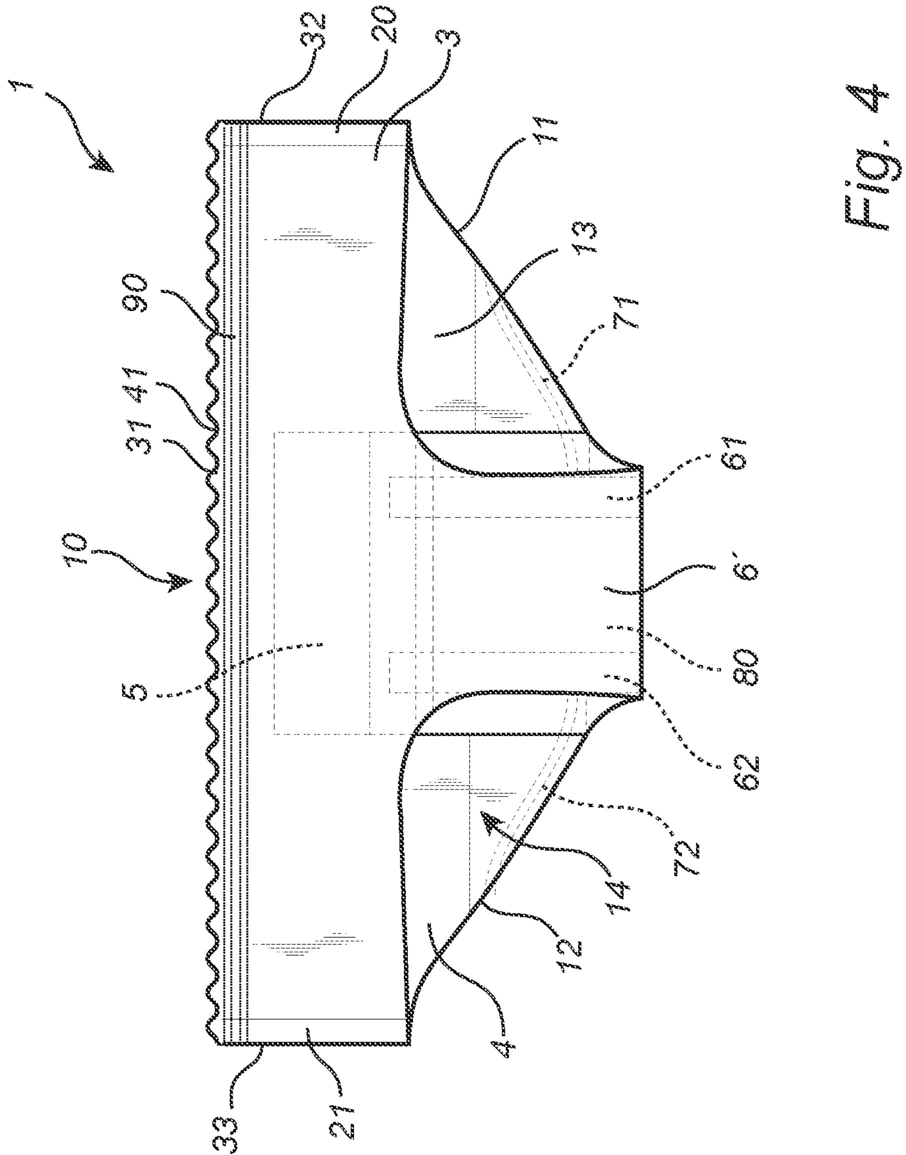
FIG. 4 shows the stretched-out pant-type article in FIG. 1A with the side seams closed.
Figure 5:
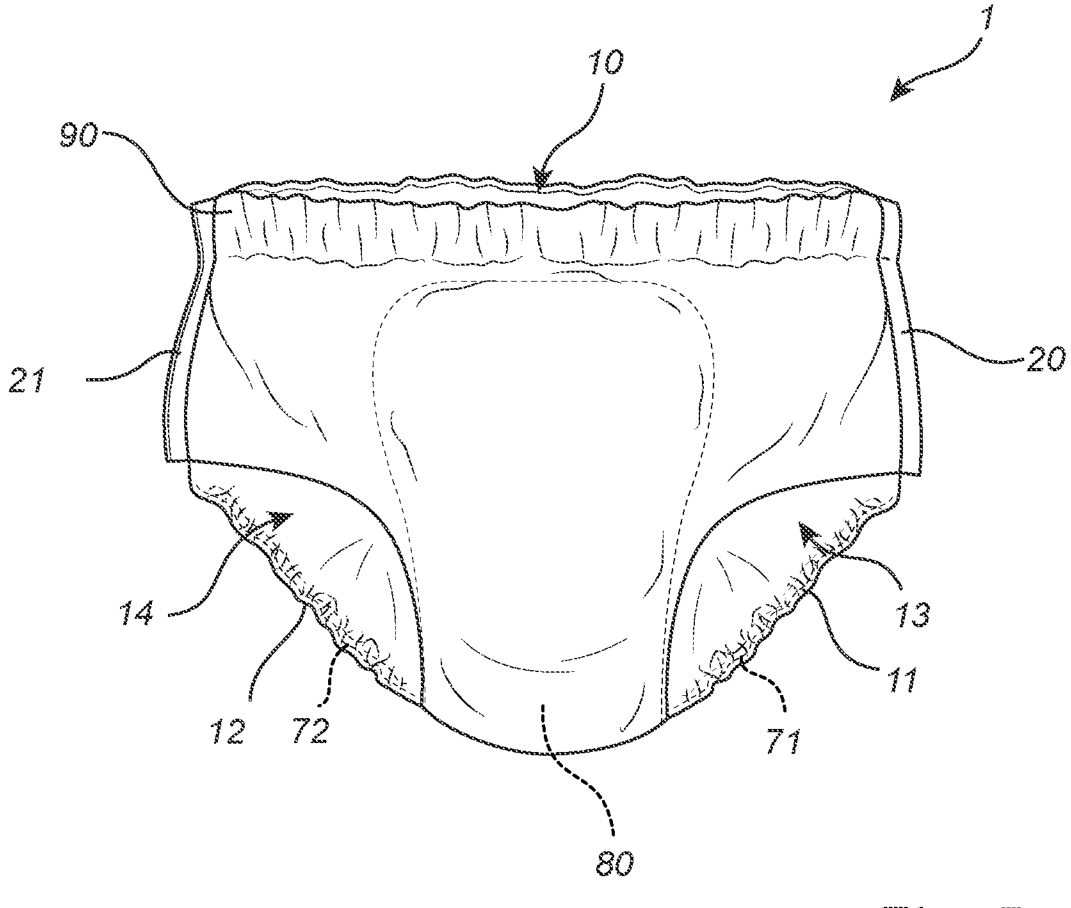
FIG. 5 shows the pant-type article in FIG. 4 in a non-stretched out condition, as it appears before use.

The first front panel side edge 32 is joined to the first rear panel side edge 42 in a first side seam 20 and the second front panel side edge 33 is joined to the second rear panel side edge 43 in a second side seam 21 to create the pant-type article 1 having a waist opening 10, a first leg opening 13 and a second leg opening 14, as shown in FIGS. 4 and 5.

FIG. 4 shows the pant-type article 1 with all elastic elements which have been stretched out during production in their fully stretched-out state, such that the pant-type article 1 appears generally two-dimensional.

FIG. 5 shows the pant-type article 1 with all elastic elements which have been stretched out during production retracted to a relaxed state, causing the web materials in the pant-type article 1 to gather.

The side seams of the pant-type articles as disclosed herein may be generally band-shaped joins which are formed by ultrasonic welding or thermowelding. To have sufficient strength to withstand the forces to which the pant-type article is exposed during donning of the article and to allow sufficient production tolerances when cutting off individual pant-type garments from a precursor web, the side seams commonly have a width in the order of 5 to 10 millimetres. It is also known to make side seams having a width less than 5 mm.

It is generally desired that a soiled pant-type garment can be easily removed without having to pull the garment down over the legs of a user. Therefore, the side seams are commonly made such that they are breakable by manual force to allow a user or a caregiver to pull apart the side seams before removing a soiled pant-type garment.

The waist opening 10 is defined by the front panel waist edge 31 and the rear panel waist edge 41. A first leg edge 11 defines the first leg opening 13 and a second leg edge 12 defines the second leg opening 14.

Figure 3:
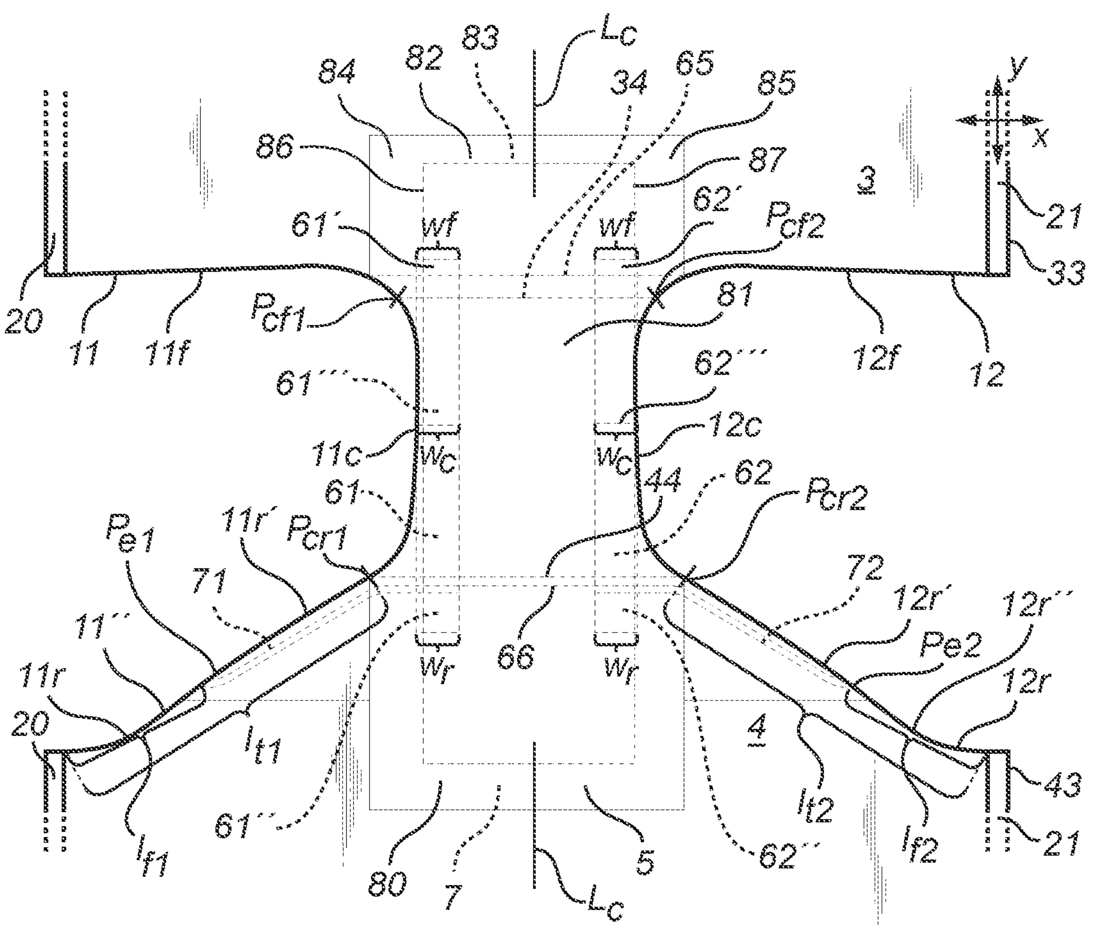
FIG. 3 shows an enlarged view of a central portion of the pant-type article in FIG. 1A.

The front body panel 3 comprises a front body panel web which is elastically stretchable at least in the transverse direction x and which provides the overall elastic stretchability of the front body panel 3. A front leg edge section 11*f*, 12*f* of each of the first and the second leg edge 11, 12, is arranged in the elastically stretchable front body panel web 3 as shown in FIG. 3.

The rear body panel 4 comprises a rear body panel web which is elastically stretchable at least in the transverse direction x and which provides the overall elastic stretchability of the rear body panel 4. A rear leg edge section 11*r*, 12*r* of each of the first and the second leg edge 11, 12, is arranged in the elastically stretchable rear body panel web 4 as shown in FIG. 3.

The crotch region 6 comprises a crotch region web, preferably a non-stretchable web material, such as a non-stretchable nonwoven. A crotch leg edge section 11*c*, 12*c* of each of the first and the second leg edge 11, 12 is arranged in the crotch web material.

The total length of the first leg edge 11 is the combined length of the front leg edge section 11*f*, the crotch leg edge section 11*c* and the rear leg edge section 11*r* of the first leg edge 11 and a total length of the second leg edge 12 is the combined length of the front leg edge section 12*f*, the crotch leg edge section 12*c* and the rear leg edge section 12*r* of the second leg edge 12.

Figure 2:
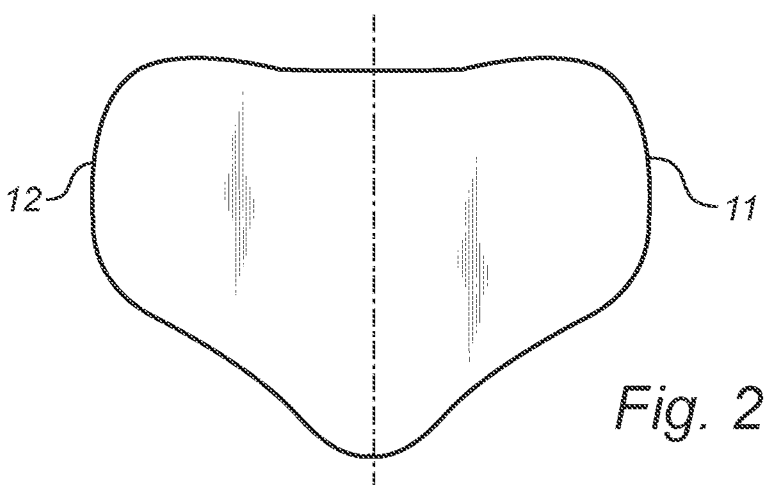
FIG. 2 shows a heart-shaped leg curve.

The first leg edge 11 and the second leg edge 12 are mirror symmetric about a longitudinally extending centre line Lc of the pant-type article 1. The first leg edge 11 and the second leg edge 12 may be described as having a shape corresponding to half of the contour of a heart-shaped area, as shown in FIG. 2. The heart-shaped contour which is shown in FIG. 2 may be obtained by shifting position of the leg edges 11, 12 in the transverse direction x until the ends of the leg edges 11, 12 may be joined to create a continuous curve.

Figure 1B:
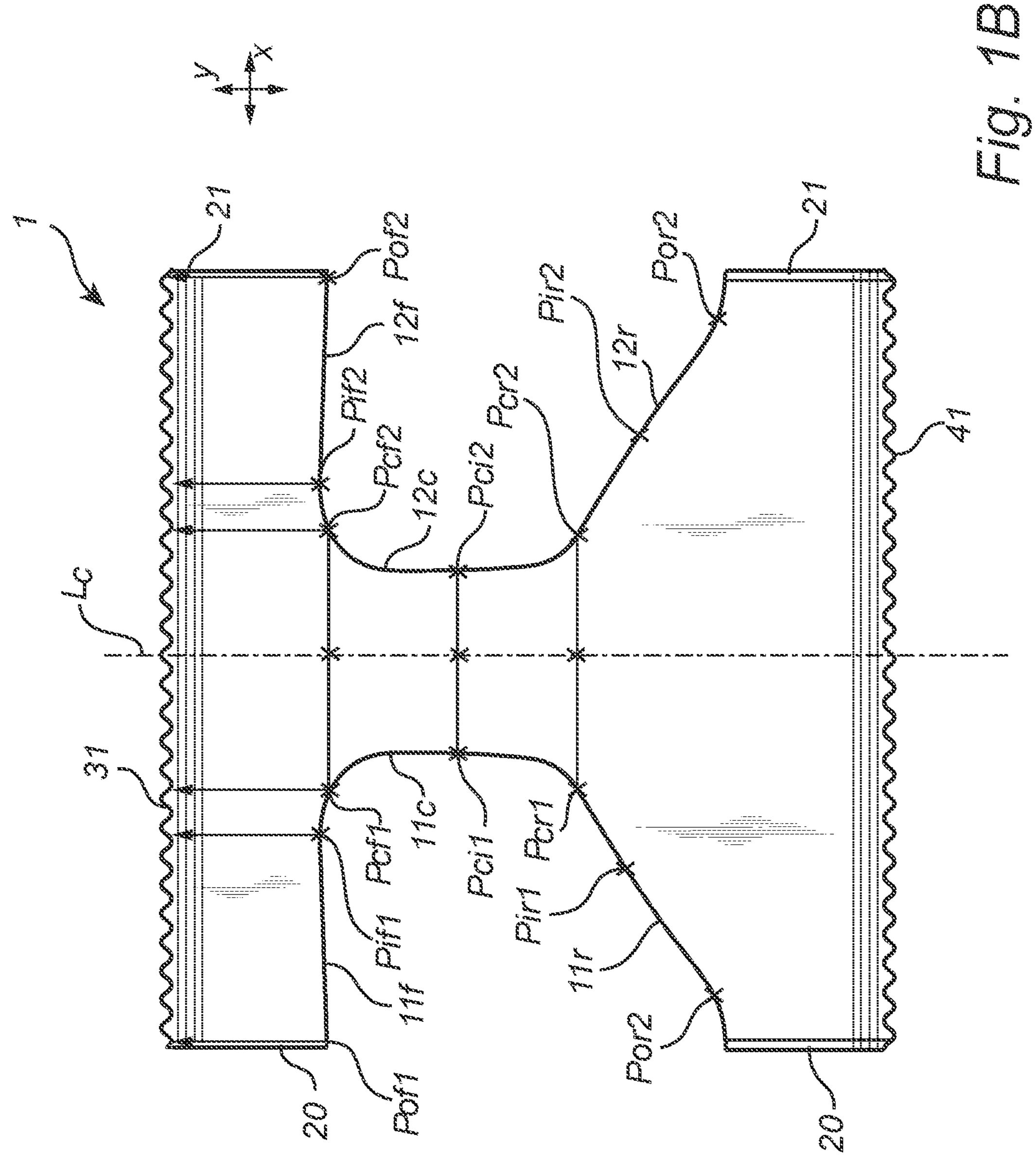
FIG. 1B shows the pant-type article in FIG. 1A without leg elastic and an absorbent assembly.

With reference to FIGS. 1A and 1B, each front leg edge section 11*f*, 12*f* has an inner point Pif1, Pif2 which is located on the front leg edge section 11*f*, 12*f* at a greater distance from the corresponding side seam 20, 21 than from the longitudinally extending centre line Lc, and an outer point Pof1, Pof2 being located on the front leg edge section 11*f*, 12*f* at the corresponding side seam 20, 21. The distance between the inner point Pif1, Pif2 and the front waist edge 31 is smaller than the distance between the outer point Pof1, Pof2 and the front waist edge 31.

Thus, the inner points Pif1, Pif2 are the points on the front leg edge sections 11*f*, 12*f* which are closest to the front waist edge 31 or in the case the front waist edge 31 is a non-straight line such as a wavy line, the inner points Pif1, Pif2 are the points on the front leg edge sections 11*f*, 12*f* which are closest to a straight line extending along and parallel to the front waist edge 31. The distance from the inner points Pif1, Pif2 to the longitudinally extending centre line Lc is smaller than the distance between each inner point Pif1, Pif2 and the corresponding the side seam 20, 21, as measured in the transverse direction x, perpendicular to the longitudinally extending centre line Lc. As disclosed herein, the distance between each inner point Pif1, Pif2 on each front leg edge section 11*f*, 12*f* and the longitudinally extending centre line Lc may be 30 to 50% of the total distance between the longitudinally extending centre line Lc and the corresponding side seam 20, 21, the distances being measured in the transverse direction x, perpendicular to the longitudinally extending centre line Lc.

The distance between the inner points Pif1, Pif2 on the front leg edge section 11*f*, 12*f* and the respective side seam 20, 21 is measured along the leg edge section 11*f*, 12*f*. The outer points Pof1, Pof2 are the end points of the front leg edge sections 11*f*, 12*f*, which are located at the side seams 20, 21, without any distance from the side seams 20, 21.

The distance between the inner and outer points Pif1, Pif2, Pof1, Pof2 on the front leg edge section 11*f*, 12*f* and the front waist edge 31 is measured perpendicular to the front waist edge 31 in the longitudinal direction y from the respective point Pif1, Pif2, Pof1, Pof2 on the front leg edge section 11*f*, 12*f* to the front waist edge 31 as indicated by arrows in FIG. 1B. In embodiments such as the embodiment shown in FIGS. 1A and 1B, having a non-linear waist edge 31, the distance is measured in the longitudinal direction y from the respective point Pif1, Pif2, Pof1, Pof2 on the front leg edge section 11*f*, 12*f* to a line extending parallel to and along the front waist edge 31.

As set out herein, the distance between the inner points Pif1, Pif2 of the front leg edge sections 11*f*, 12*f* and the front waist edge 31 is the smallest distance between the front leg edge sections and the front waist edge 31 corresponding to the highest point on the front leg edge sections. Each front leg edge section 11*f*, 12*f* of the disposable pant-type articles as disclosed herein has only a single such highest point Pif1, Pif2 where the distance between the front leg edge section 11*f*, 12*f* and the front waist edge 31 is the smallest distance between the front leg edge section 11*f*, 12*f* and the front waist edge 31.

As set out herein, the distance between the outer points Pof1, Pof2 of the front leg edge sections 11*f*, 12*f* and the front waist edge 31 in a part of the front leg edge which is defined between the inner points Pif1, Pif2 of the front leg edge sections 11*f*, 12*f* and the side seams 20, 21 is the greatest distance between the front leg edge sections 11*f*, 12*f* and the front waist edge 31 corresponding to the lowest point on the front leg edge sections 11*f*, 12*f* within this part of the front leg edge sections 11*f*, 12*f*. Each front leg edge section 11*f*, 12*f* of the disposable pant-type articles as disclosed herein has only a single such lowest point Pof1, Pof2 in the part of the front leg edge sections 11*f*, 12*f* which is defined between the inner points Pif1, Pif2 of the front leg edge sections 11*f*, 12*f* and the side seams 20, 21, where the distance between the front leg edge section 11*f*, 12*f* and the front waist edge 31 is the greatest distance between the front leg edge section 11*f*, 12*f* and the front waist edge 31.

Figure 1C:
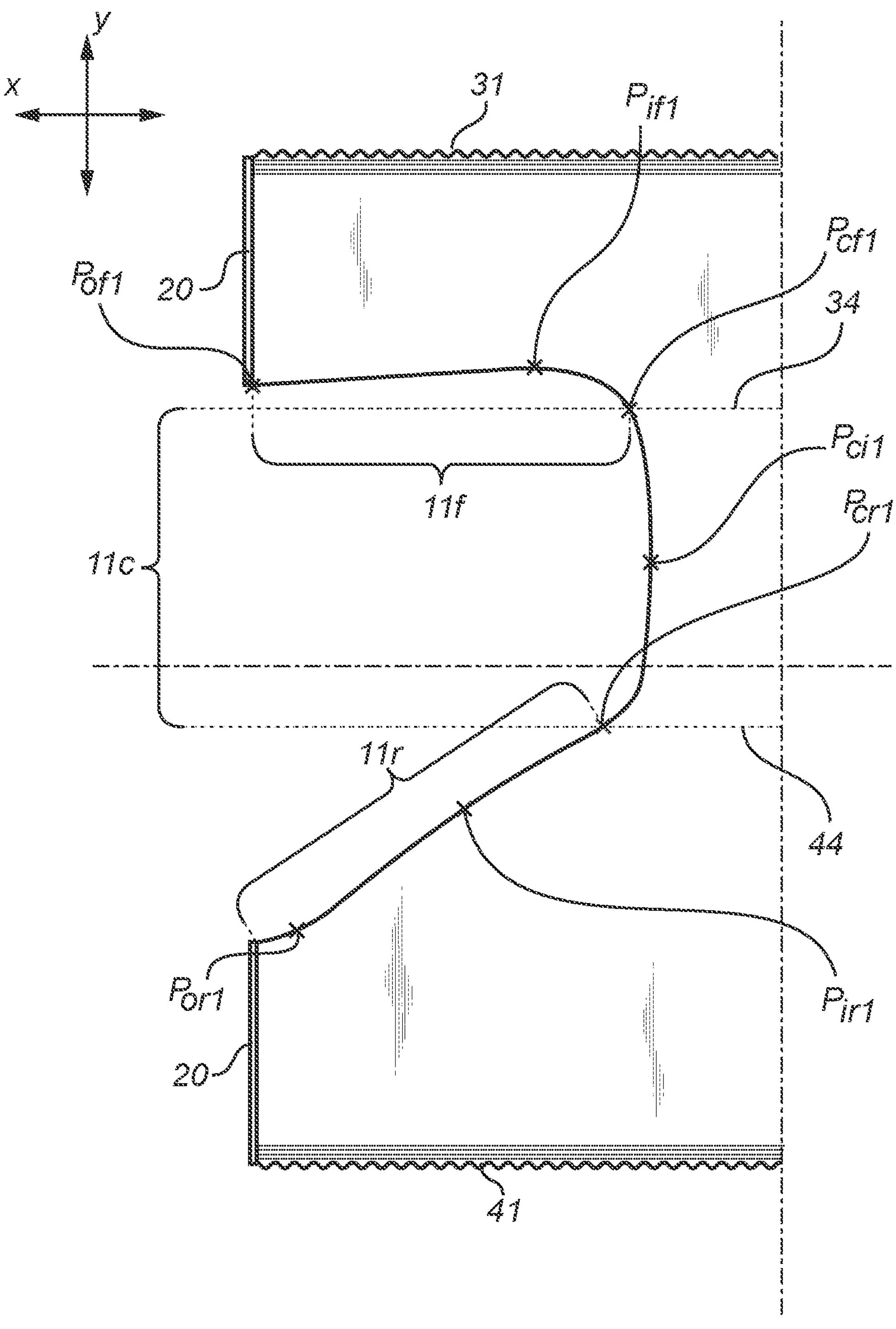
FIG. 1C shows a detailed view of a first leg edge in the pant-type article in FIG. 1A.

With reference to FIG. 1C which shows a detailed view of the first leg edge 11 of the pant-diaper 1A, the rear leg edge section 11*r* has a convex curved buttocks portion with a curve maximum located at an inner point Pir1 on the rear leg edge section 11*r*.

The rear leg edge section 11*r* further has a first transition point Por1, located closer to the first side seam 20 than the inner point Pir1 on the first rear leg edge section 11*r*. At the first transition point Por1, the convex curved buttocks portion of the rear leg edge section changes into a concavely curved hip portion of the rear leg edge section. The first transition point Por1 between the convex buttocks portion and the concave hip portion is shown in FIG. 1C to be located at a distance from the first side seam 20 which may be from 30 millimetres to 80 millimetres from the side seam 20. A corresponding second transition point Por2 is found on the second rear leg edge section 12*r*, as is indicated in FIG. 1A.

The distance between the inner points Pir1, Pir2, on the rear leg edge section 11*r*, 12*r* and the respective side seam 20, 21 and the distance between the transition points Por1, Por2 and the respective side seam 20, 21 is measured along the leg edge section 11*r*, 12*r*.

Each crotch leg edge section 11*c*, 12*c* has an intermediate point Pci1, Pci2 located between the front crotch edge 34 and the rear crotch edge 44, which intermediate point Pci1, Pci2 is closer to the longitudinal centre line Lc than a front endpoint Pcf1, Pcf2 of the crotch leg edge section 11*c*, 12*c* where the leg edge 11, 12 intersects with the front crotch edge 34. The intermediate point on the crotch leg edge section 11*c*, 12*c* is also closer to the longitudinal centre line Lc than a rear endpoint Pcr1, Pcr2 of the crotch leg edge section 11*c*, 12*c* where the leg edge 11, 12 intersects with the rear crotch edge 44. The distance between the front endpoints Pcf1, Pcf2 of the crotch leg edge sections 11*c*, 12*c* and the front waist edge 31 may be greater than the distance between the outer points Pof1, Pof2 of the front leg edge sections 11*f*, 12*f* and the front waist edge 31, as is shown in the figures, such that the front endpoints Pcf1, Pcf2 of the crotch leg edge sections 11*c*, 12*c* are placed lower than the outer points Pof1, Pof2 of the front leg edge sections 11*f*, 12*f*.

The distance between the points Pci1, Pci2, Pcf1, Pcf2, Pcr1, Pcr2 on the crotch leg edge section 11*c*, 12*c* and the longitudinal centre line Lc is measured in the transverse direction x from the respective Pci1, Pci2, Pcf1, Pcf2, Pcr1, Pcr2 on the crotch leg edge section 11*c*, 12*c* to the longitudinal centre line Lc, as indicated by arrows in FIG. 1B.

The rear leg edge section 12*r* of the second leg edge 12 of the pant-type article 1 in FIG. 1A has a shape corresponding to the rear leg edge section 11*r* of the first leg edge 11.

A first crotch elastic member 61 is arranged extending in the longitudinal direction y along the first leg edge 11 between the front panel crotch edge 34 and the rear panel crotch edge 44 and a second crotch elastic member 62 is arranged extending in the longitudinal direction y along the second leg edge 12 between the front panel crotch edge 34 and the rear panel crotch edge 44. The crotch elastic members 61, 62 are constituted by band-shaped strips of elastic film which are applied to the pant-type article in a stretched condition and form functional leg elastic in the crotch region of the pant-type article 1.

The crotch leg edge sections 11*c*, 12*c* of the first and second leg edges 11, 12 are concavely curved and extend partly in the corresponding crotch elastic member 61, 62.

Figure 6:
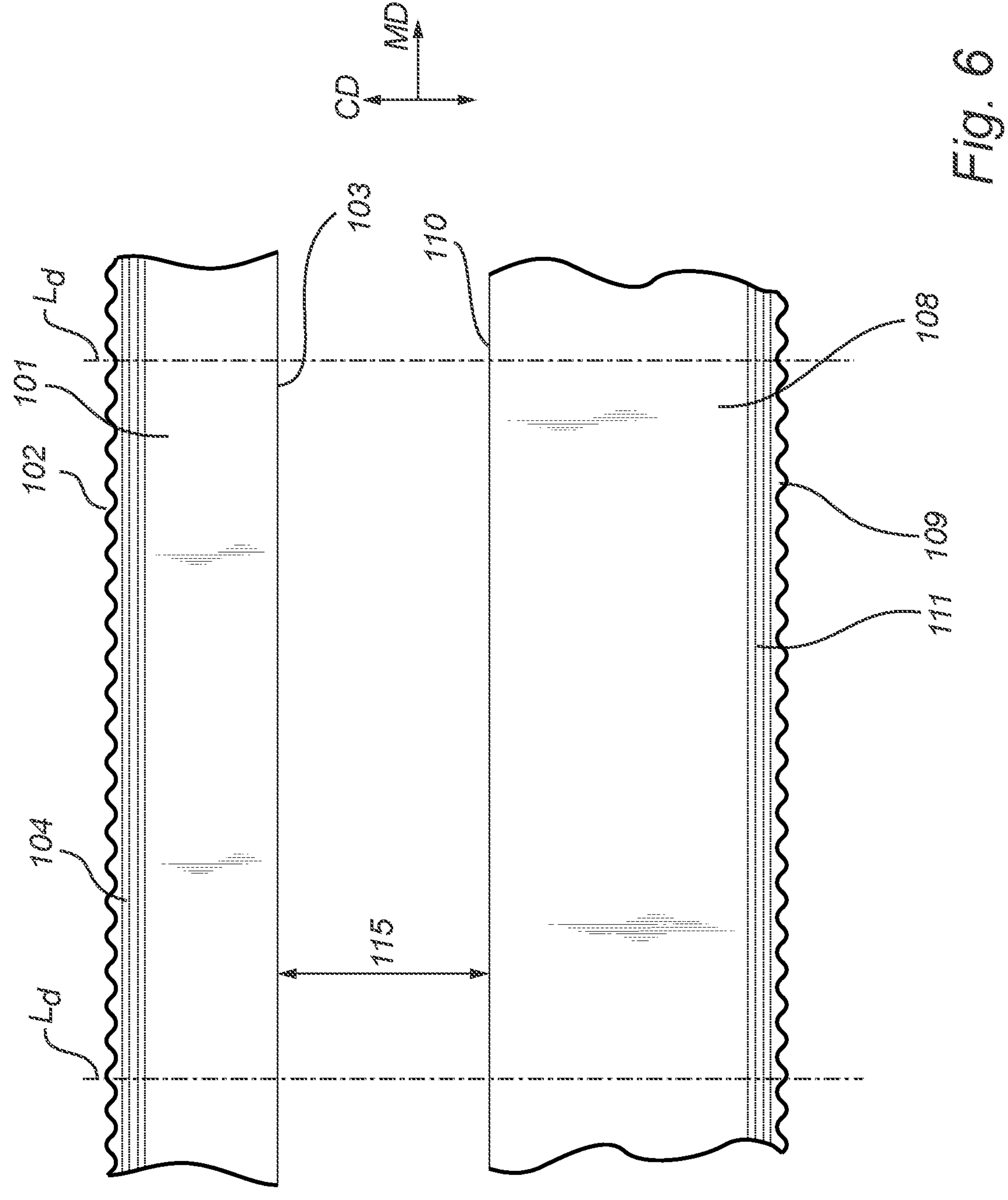
FIGS. 6-11 show planar views of a section of a chassis web in progressing stages of production.

The crotch leg edge sections 11*c*, 12*c* are cut with a slightly concave curvature, as seen in FIG. 6 such that also the crotch elastic members 61, 62 have a somewhat modified band-shape with a concave cut edge along at a part of the crotch leg edge sections 11*c*, 12*c*. The cut into the crotch elastic members 61, 62 need not be made with a continuous curvature and may have any useful shape.

It may be desirable that all sections 11*f*, 12*f*, 11*c*, 12*c*, 11*r*, 12*r* of the first leg edge 11 and the second leg edge 12 are cut in a coherent elastic material, such that an elastic film, an elastic nonwoven or an elastic foam material, with a primary direction of the cut being in the direction of stretchability of the elastic material, i.e., the front and rear leg edge sections 11*f*, 12*f*, 11*r*, 12*r* are cut primarily in the transverse direction x and the crotch leg edge sections 11*c*, 12*c* are cut primarily in the longitudinal direction y.

The crotch elastic members 61, 62 each have a front end portion 61', 62' at the front panel crotch edge 34, a rear end portion 61", 62" at the rear panel crotch edge 44 and an intermediate portion 61'", 62'" between the front end portion 61', 62' and the rear end portion 61", 62". The front end portion 61', 62' of each of the first and the second crotch elastic members 61, 62 overlaps with and is attached to the front body panel 3 and the rear end portion 61", 62" of each of the first and the second crotch elastic members 61, 62 overlaps with and is attached to the rear body panel 4. The end portions 61', 62', 61", 62" of the crotch elastic members 61, 62 may be non-tensioned parts of the crotch elastic members 61, 61. Non-tensioned end portions 61', 62', 61", 62" of the crotch elastic members 61, 62 may each have a length of from 5% to 8% of the total length of the crotch elastic member, including the length of the end portions 61', 62', 61", 62" and the pre-tensioned intermediate portion 61'", 62'" located between the end portions 61', 62', 61", 62".

The crotch leg edge sections 11*c*, 12*c* are cut with a concave curvature into the crotch elastic members 61, 62, whereby the front end portions 61', 62' of the crotch elastic members 61, 62 and the rear end portions 61", 62" of the crotch elastic members 61, 62 have a greater width in the front and rear end portions 61', 62', 61", 62" of the crotch elastic members 61, 62 than in the intermediate portion 61'", 62'" of the crotch elastic members.

In the pant-type article 1 which is shown in the Figures, the width wf of the front end portion 61', 62' is equal to the width wr of the rear end portion 61", 62". A suitable ratio between the width of the end portions wf, wr and the smallest width wc of the intermediate portion may be from 1:0.5 to 1:0.9.

The crotch region 6 is formed by a crotch panel 6' which is attached with a first side edge 65 of the crotch panel 6' to the front body panel 3 along the front panel crotch edge 34, and with a second side edge 66 of the crotch panel 6' attached to the rear body panel 4 along the rear panel crotch edge 44. The attachments between the crotch panel and the front and rear panels are made as overlap seams.

Alternatively, or in addition to applying a crotch panel in the crotch region as shown in the Figures, the crotch region may comprise a portion of a web material, such as an inner or outer cover web material of the pant-type article which extends continuously in the longitudinal direction from the front panel waist edge to the rear panel waist edge and bridges a gap between the front panel crotch edge and the rear panel crotch edge. The portion of the continuous cover web material which is applied in the crotch region constitutes the crotch web material.

A first reinforcing elastic feature 71 is arranged on the elastically stretchable rear body panel 4 along the rear leg edge section 11*r* of the first leg edge 11 and a second reinforcing elastic feature 72 is arranged on the elastically stretchable rear body panel 4 along the rear leg edge section 12*r* of the second leg edge 12. The first reinforcing elastic feature 71 extends along a first part 11*r*' of the rear leg edge section 11*r* of the first leg edge 11 in a direction away from the longitudinal centre line Lc of the pant-type article 1 towards the first side seam 20 and has an end point Pe1 on the rear leg edge section 11*r* of the first leg edge 11, with a second part 11*r*" of the rear leg edge section 11*r* of the first leg edge 11 being free from the first reinforcing elastic feature 71.

The second part 11*r*" of the rear leg edge section 11*r* of the first rear leg edge 11 which is free from reinforcing elastic, has a length lf1, as measured along the first leg edge 11 from the end point Pe of the first reinforcing elastic feature 71 to the first side seam 20 which is from 25% to 75% of a total length lt1 of the rear leg edge section 11*r* of the first leg edge 1.

The second reinforcing elastic feature 72 extends along a first part 12*r*' of the rear leg edge section 12*r* of the second leg edge 12 in a direction away from the longitudinal centre line Lc of the pant-type article 1 towards the second side seam 21 and has an end point Pe2 on the rear leg edge section 12*r* of the second leg edge 12, with a second part 12*r*" of the rear leg edge section 12*r* of the second leg edge 12 being free from the second reinforcing elastic feature 72, the second part 12*r*" of the rear leg edge section 12*r* of the second leg edge 12 having a length lf2 as measured along the second leg edge 12 from the end point Pe2 of the second reinforcing elastic feature 72 to the second side seam 21 which is from 25% to 75% of a total length lt2 of the rear leg edge section 12*r* of the second leg edge 12.

The first and second reinforcing elastic features 71, 72 are attached to the rear end portions 61", 62" of the crotch elastic members 61, 62, the rear end portions 61", 62" of the crotch elastic members 61, 62 suitably being non-tensioned portions of the crotch elastic members 61, 62, serving as non-extensible inner anchoring areas for the reinforcing elastic features 71, 72.

With reference to FIGS. 1 and 3, the pant-type article 1 further comprises an absorbent assembly 80 comprising an absorbent core 81, a liquid permeable topsheet 82 and a liquid impermeable backsheet 83, the absorbent core 81 being enclosed between the liquid permeable topsheet 82 and the liquid impermeable backsheet 83.

The absorbent core 81 which is shown in the figures has a rectangular design. However, the disclosure is not limited to rectangular cores and it is to be understood that the absorbent core may have any useful shape, such as hourglass shape T-shape, etc., as known in the art.

The absorbent assembly 80 is applied on the inner surface of the pant-type article 1, the inner surface being the surface which is intended to be facing the wearer when the pant-type article 1 is being worn. The absorbent assembly 80 covers the pre-tensioned crotch elastic members 61, 62. The inner surface of the absorbent assembly is formed by the liquid permeable topsheet 82 and may optionally include barrier cuffs (not shown) extending along the side edges of the absorbent assembly 80.

A part of each leg edge 11, 12 which extends in the crotch region 6 has been formed by a cut through the material in the crotch panel 6', through the corresponding crotch elastic member 61, 62 and through a peripheral edge portion 84, 85 of the absorbent assembly 80.

The peripheral edge portions 84, 85 of the absorbent assembly 80 are formed by edge parts of the liquid permeable topsheet 82 and the liquid impermeable backsheet 83 which extend in the transverse direction x outward of the peripheral side edges 86, 87 of the absorbent core 81 of the absorbent assembly 80.

As disclosed herein, the topsheet 82 and the backsheet 83 may both extend beyond the periphery of the absorbent core 81 and may be joined to each other in an edge seal extending along the periphery of the absorbent core outward of a peripheral edge of the absorbent core. In the embodiment shown in the FIGS., the topsheet 82 and the backsheet 83 are only joined in edge seals in the peripheral edge portions 84, 85 which extend along the peripheral side edges 86, 87 of the absorbent core 81. However, such edge seals may be arranged along the complete periphery of the absorbent core 81, i.e., also along the transverse end edges of the absorbent core 81. Furthermore, the peripheral edge portion 84, 85 of the absorbent assembly 80 may be formed by only one of the topsheet and the backsheet, as set out herein.

The absorbent assembly 80 covers the crotch elastic members 61, 62 on the inner surface of the pant-type article 1 with the peripheral edge portions 84, 85 of the absorbent assembly 80 which are formed by the topsheet 82 and the backsheet 83 overlying a portion of the respective crotch elastic member 61, 62 adjacent the corresponding crotch leg edge section 11*c*, 12*c*.

As set out herein, the crotch leg edge sections 11*c*, 12*c* are formed by cuts having a concave curvature and which have been made through the superposed crotch web material, the crotch elastic members 61, 62 and the topsheet 82 and the backsheet 83 in the peripheral edge portion 84, 85 along each crotch leg edge section 11*c*, 12*c*. As shown in FIGS. 1 and 2, the cuts have been made such that a small part of each crotch elastic member 61, 62 has been cut away in the intermediate portion 61'", 62'" of the crotch elastic member 61, 62, providing the intermediate portion 61'", 62'" of the crotch elastic member 61, 62 with a concavely curved edge which is coterminous with the simultaneously formed cut edges of the crotch web material, the topsheet 82 and the backsheet 35. In the embodiment shown in the figures, the crotch web material is the web material which forms the crotch panel 6'. However, in other embodiments, the crotch web material may be formed by a portion of an outer cover web, as set out herein.

An absorbent core 81 as disclosed herein may comprise any conventional material suitable for absorbing discharged bodily wastes, such as cellulosic fluff pulp, tissue layers, highly absorbent polymers (super absorbents), absorbent foam materials including hydrogel-foam material, absorbent nonwoven materials, or the like. The absorbent core can comprise non-absorbent components such as stiffening elements, shaping elements, binders, etc. Various types of liquid-receiving and liquid distribution elements can also be included in the core.

The liquid permeable topsheet 82 may comprise or consist of a nonwoven material. Other suitable topsheet materials include tow fibres, porous foams, apertured plastic films and laminates and combinations of such materials. The materials which are best suited as topsheet materials are soft and non-irritating to the skin, are readily penetrated by body fluids, and display low rewet.

The liquid impermeable backsheet 83 may consist of a thin plastic film, e. g. a polyethylene or polypropylene film, a nonwoven material coated with a liquid impervious material, a hydrophobic nonwoven material which resists liquid penetration or laminates of plastic film and nonwoven. The backsheet material may be breathable to allow vapour to escape from the absorbent body, while still preventing liquids from passing through the backsheet material.

The topsheet and backsheet may be connected to each other for example by adhesive bonding, gluing or welding by heat or ultrasonically. The topsheet and/or the backsheet may further be attached to the absorbent core by any method known in the art, such as adhesive, heat-bonding, welding, needling, etc.

The pant-type articles as disclosed herein may be of the kind shown in the Figures and having a two-part chassis with a crotch panel which is connected to the front panel along the front panel crotch edge and which is connected to the rear panel along the rear panel crotch edge. Alternatively, the pant-type article may have a unitary chassis having a non-elastic outer or inner cover web extending the full distance between the front panel waist edge and the rear panel waist edge, the cover web constituting a non-elastic layer of each of the front panel and the rear panel and constituting the crotch web material in the crotch region of the pant-type article.

The elastically stretchable front body panel and the elastically stretchable rear body panel may comprise or consist of a stretchbonded laminated elastic web material.

Suitable stretch-bonded laminates may comprise nonwoven material layers or webs such as spunbond, air laid, wet laid, carded, electro spun or meltblown nonwovens. The nonwoven material may be bonded by any suitable technique, such as by needling, hydroentangling, ultrasonic welding, or thermobonding.

The fibers of the nonwoven materials used herein may be man-made fibers, natural fibers or mixtures of man-made and natural fibers. Man-made fibers include mono-component, bi-component and multicomponent fibers of polymers such as polyolefins, polyesters, polyacrylates, etc., as well as regenerated fibers such as viscose fibers and modal fibers. Natural fibres are for instance cellulosic fibres such as pulp fibers, cotton fibers, flax, hemp, etc.

The pant-type article 1 as disclosed herein may have an elastic waist feature 90 arranged along the waist opening 10. An elastic waist feature 90 may be formed by one or more elastic elements extending parallel with the front panel waist edge 31 and the rear panel waist edge 41. The elastic waist element or elements may be incorporated in the front body panel 3 and the rear body panel 4 or may be applied as a separate waistband which is attached to the front panel waist edge 31 and the rear panel waist edge 41. The pant-type article 1 which is shown in the Figures has an elastic waist feature 90 which extends around the full circumference of the waist opening 10. However, an elastic waist feature may be arranged only along a part of the waist opening, such as only along the rear panel waist edge, only along the front panel waist edge or along a part of one or both the front and the rear panel waist edge which part has a length which is less than the full length of the corresponding panel waist edge.

The elastic material in elastic elements arranged along the leg openings 13, 14 and the waist opening 10 as disclosed herein may be any suitable elastic material such as natural or synthetic rubber, thermoplastic elastomers, such as thermoplastic polyurethane or styrene block co-polymers or elastane, also referred as to spandex (polyurethane-polyurea copolymer). The elastic elements may be of the elastane type that is available under the trade name "LYCRA", but any suitable elastic thread may be used. The threads may have a linear mass density, dtex, of about 80-1200 dtex.

The nonwoven web-materials used in the pant-type articles as disclosed herein may comprise thermoplastic material. The nonwoven web-materials will typically be incorporated in joins and seams in the pant-type article and it is desirable that the nonwoven webs be weldable by heat or by ultrasonic welding processes. Examples of suitable polymers for use in the fibrous nonwoven webs as disclosed herein are polyethylene polypropylene and other polyolefin homopolymers and copolymers and polyesters. The weldable nonwoven webs have a high content of thermoplastic component and preferably contain at least 50% thermoplastic fibres and more preferably at least 80% thermoplastic fibres.

The elastic material used in the front and rear body panels is preferably a breathable elastic film such as an apertured or microporous elastic film. The elastic film may have a basis weight of between 20 and 80 g/m$^2$, preferably between 20 and 60 g/m$^2$. The elastic web may be of any suitable elastic polymer, natural or synthetic. Some examples of useful materials for the elastic web are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. The total basis weight of the stretchbonded elastic laminate web is preferably between 40 and 100 g/m$^2$, more preferably not more than 90 g/m$^2$.

The contour of the rear leg edge sections as described in connection with the FIGS., as well as the provision of crotch elastic members, reinforcing rear elastic features and waist elastic are optional to the pant-type absorbent articles as disclosed herein.

A continuous method of producing disposable pant-type articles as disclosed herein will be described with reference to FIGS. 6-13.

FIG. 6 shows a continuous elastic front panel web 101 which is being advanced in a machine direction MD. The front panel web 101 is advanced in the machine direction MD while being stretched in the machine direction MD such that the front panel web 101 is tensioned in the machine direction MD.

The front panel web 101 has a front waist edge 102 and an opposing front crotch edge 103.

FIG. 6 further shows a continuous elastic rear panel web 108 which is being advanced in the machine direction MD parallel to the elastic front panel web 101. The rear panel web 108 is advanced in the machine direction MD while being stretched in the machine direction MD such that the rear panel web 108 is tensioned in the machine direction MD.

The rear panel web 108 has a rear waist edge 109 and an opposing rear crotch edge 110. The rear panel web 108 is spaced apart from the front panel web 101 in a cross machine direction CD, perpendicular to the machine direction MD, with a gap 115 in the cross machine direction CD between the crotch edge 103 of the front panel web 101 and the crotch edge 110 of the rear panel web 108.

A front waist elastic member 104 is arranged along the front waist edge 102 and a rear waist elastic member 111 is arranged along the rear waist edge 109. The waist elastic members 104, 111 have been attached to the front panel web 101 and the rear panel web 108 prior to the production step shown in FIG. 6 e.g., by a method as disclosed in WO 2017/044013 A1 and WO 2017/044014 A1. The method in WO 2017/044013 A1 and WO 2017/044014 A1 starts from a base web to which a continuous waistband component is attached, whereafter the base web is cut in two parts along a cutting line extending in the machine direction and severing both the base web and the waistband component along the cutting line. By dividing the base web in two parts there is formed a first panel web having a first portion of the waistband component attached thereto and a second panel web having a second portion of the waistband component attached thereto. The two web parts are subsequently shifted in the cross machine direction such that the cut edges of the web parts along which the parts of the waistband component are attached are arranged facing away from each other. When the web parts are further processed in the method as disclosed herein, the cut edge of the first panel web forms the front waist edge 102 of the front panel web 101 and the cut edge of the second panel web forms the rear waist edge 109 of the rear panel web 108 as shown in FIG. 6. The divided waistband component forms the front waist elastic member

104 and the rear waist elastic member 111 on the respective front panel web 101 and rear panel web 108.

The method in WO 2017/044013 A1 and WO 2017/044014 A1 results in a front waist elastic member 104 which coincides with the front waist edge 102 of the front panel web 101 and a rear waist elastic member 111 which coincides with the rear waist edge 109 of the rear panel web 108. In the example shown in FIGS. 6-13, the front waist edge 102 and the rear waist edge 109 have matching sinusoidal configurations. It is to be understood that the waist edges need not have the undulating configuration shown in the Figures and that any other configuration may be used such as a straight edge, a zig-zag edge, etc. Furthermore, it is to be understood that other methods for attaching a waistband member to the front and rear panel webs may be used. The front waistband member may alternatively be attached with an edge seam along the front waist edge of the front panel web and the rear waistband member may be attached with an edge seam along the rear waist edge of the rear panel web. In such embodiments, the waistband members extend in the cross machine direction CD outward of the waist edge of the corresponding panel web. Another conceivable arrangement of the waistband members is to attach them slightly inward of the waist edges of the panel webs. In such embodiments, each waistband member is fully overlapping with the corresponding panel web, with a small edge portion of the panel web extending in the cross machine direction CD a distance in the order of 2 to 15 mm outward of the waist edge of the panel web.

Waistband members which are attached to the front panel web and the rear panel web by other methods than the method disclosed in WO 2017/044013 A1 and WO 2017/044014 A1, may be attached during any suitable stage of the method as disclosed herein or may be attached prior to the stage shown in FIG. 6. It is also to be understood that the waist elastic members as disclosed herein are optional to the method and the disposable pant-type articles as disclosed herein.

The waist elastic members may comprise or consist of any suitable elastic material or elasticated material as known in the art including elastic threads, elastic film, elastic nonwoven and elastic foam. Furthermore, an elastic member may be applied in the form of multiple elongate elastic elements, as a single band of elastic or elasticated material e.g., an elastic laminate. In all instances, the elastic member is a component of a chassis web or a disposable pant-type article as disclosed herein, which is separate and distinct from other elastification of the chassis web of the pant-type article such as leg elastic or body elastic.

Figure 7:
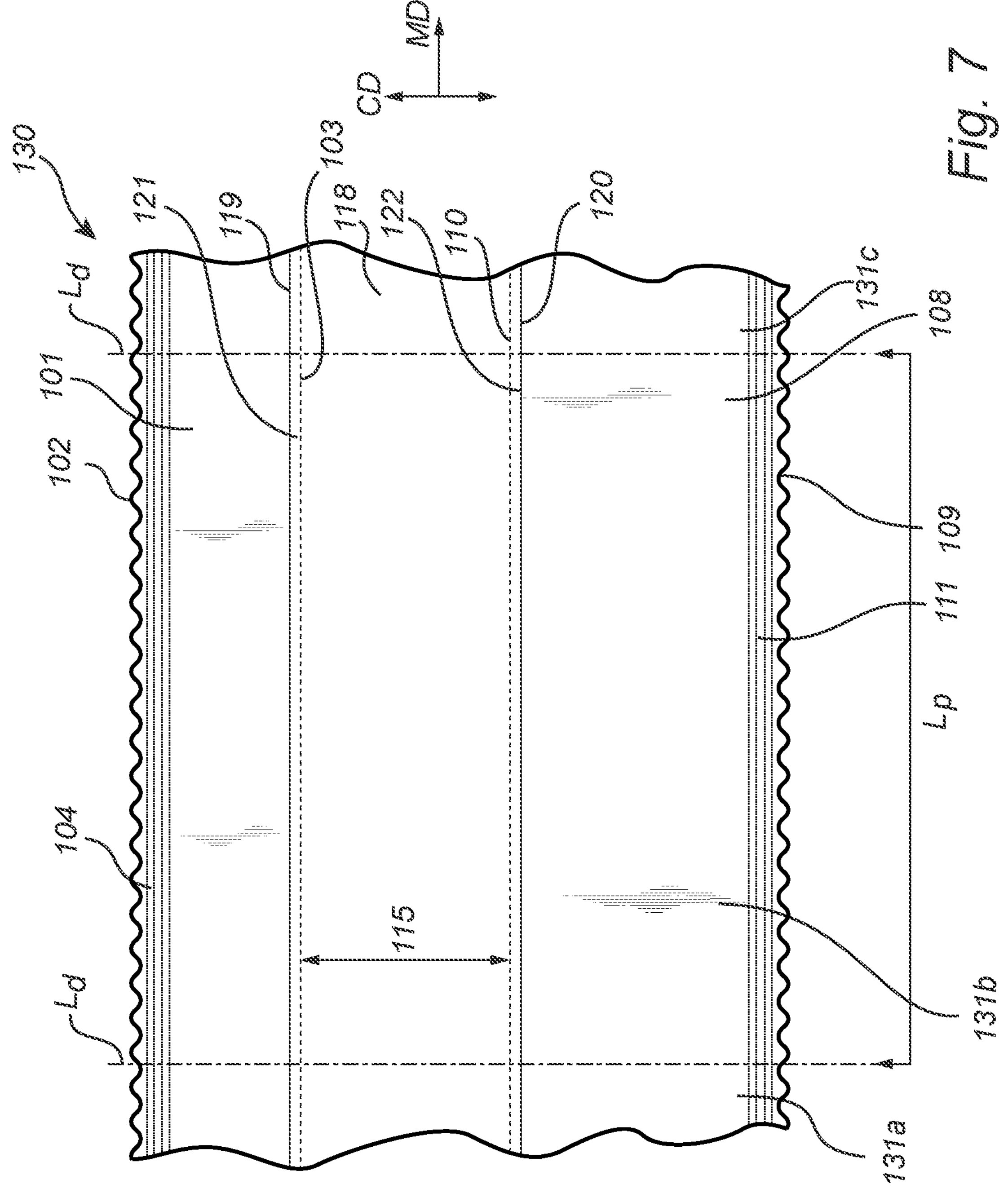

A non-elastic continuous crotch panel web 118 having a first side edge 119 and an opposing second side edge 120 is then advanced in the machine direction MD and the first side edge 119 of the crotch panel web 118 is attached in a first overlap seam 121 along the crotch edge 103 of the tensioned front panel web 101 and the second side edge 120 of the crotch panel web 118 is attached in a second overlap seam 122 along the crotch edge 110 of the tensioned rear panel web 108, as shown in FIG. 7. The crotch panel web 118 bridges the gap 115 between the front panel web 101 and the rear panel web 108 to form a coherent chassis web 130 of interconnected precursor articles 131*a*, 131*b*, 131*c*, being delimited by dividing lines Ld extending in the cross machine direction CD, each precursor article 131*a*, 131*b*, 131*c* having a pitch-length Lp in the machine direction MD between the dividing lines Ld. The pitch-length Lp of the precursor articles 131*a*, 131*b*, 131*c* remains the same until the final step of the method as disclosed herein, when individual pant-type articles are severed from the chassis web 130.

Figure 8:
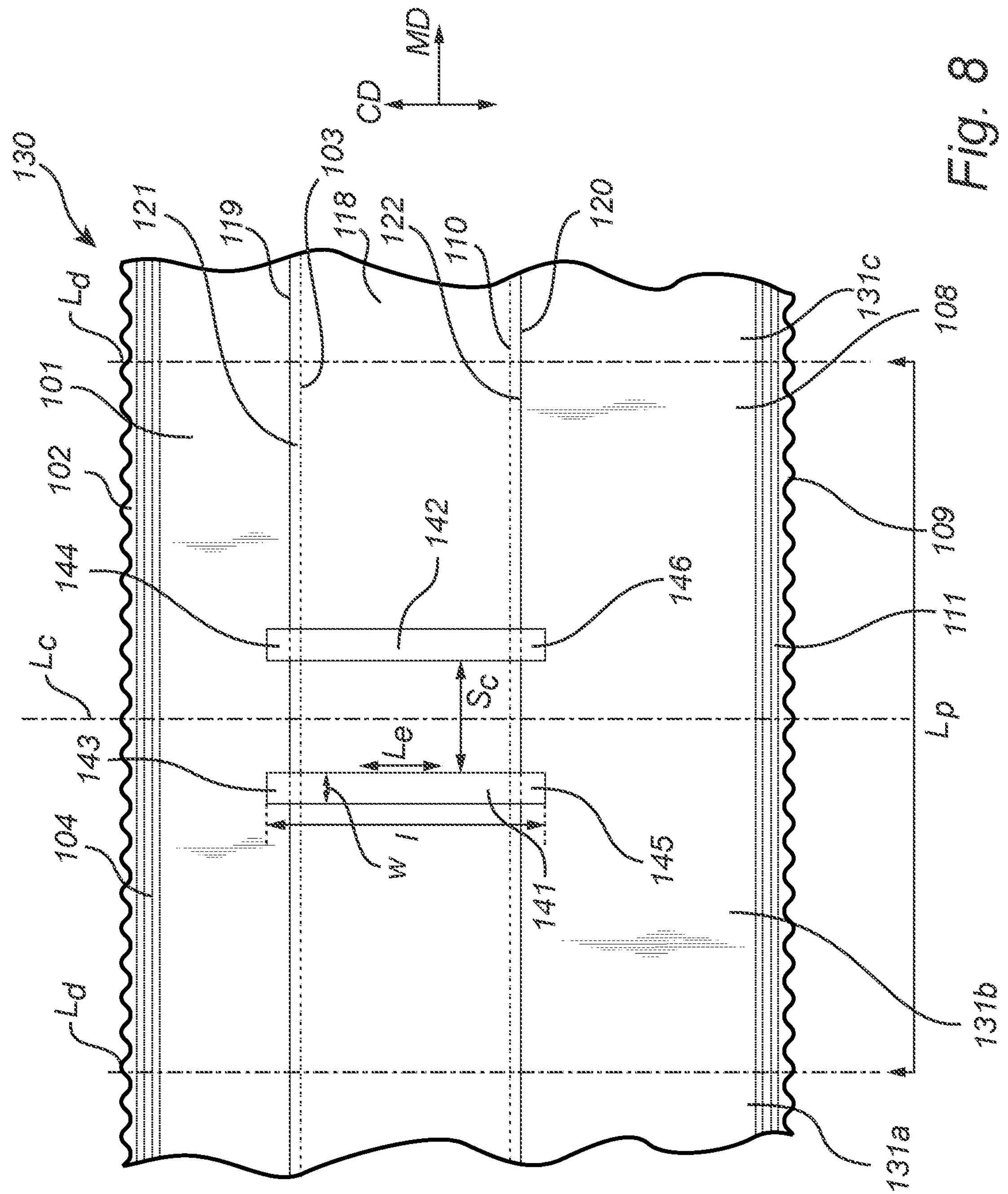

With reference to FIG. 8, a pair of crotch elastic members 141, 142 is provided consisting of a first band-shaped crotch elastic member 141 and a second band-shaped crotch elastic member 142.

Each crotch elastic member 141, 142 is stretched in a longitudinal direction $L_e$ of the crotch elastic member and the longitudinal direction $L_e$ of the crotch elastic member 141,142 is aligned with the cross machine direction CD of the moving chassis web 130. Each stretched crotch elastic member 141, 142 is then attached to the chassis web 130 while keeping the crotch elastic member 141, 142 stretched and aligned with the cross machine direction CD. The pair of crotch elastic members is attached to the chassis web 130 with the first crotch elastic member 141 being spaced apart from the second crotch elastic member 151 with a crotch spacing Sc in the machine direction and are symmetrically placed on each side of a precursor article centerline Lc extending in the cross machine direction CD. The pairs of crotch elastic members of the precursor articles 131*a*, 131*b*, 131*c* are spaced apart in the machine direction with an article spacing corresponding to the pitch-length of the precursor articles 131*a*, 131*b*, 131*c*.

In the moving chassis web 130 which is shown in the Figures, a first end portion 143,144 of each of the first and the second crotch elastic members 141,142 is overlapped with and attached to the tensioned front panel web 101 and a second end portion 145,146 of each of the first and the second crotch elastic members 141, 142 is overlapped with and attached to the tensioned rear panel web 108.

When stretching and applying the stretched crotch elastic members 141, 142 to the chassis web, the first and second end portions 143, 144, 145, 146 of the crotch elastic members 141, 142 may be held in movable clamps in a stretching device (not shown). The clamped end portions 143, 144, 145, 146 are not subjected to stretching and are applied and attached to the chassis web in a non-tensioned condition.

The stretched crotch elastic members 141, 142 may have a width w as measured in the machine direction MD in the range of from 15 mm to 50 mm and a length l as measured in the cross machine direction in the range of from 150 mm to 350 mm.

In a preferred embodiment of the method as disclosed herein the elastic members comprise or consist of elastic film.

Figure 9:
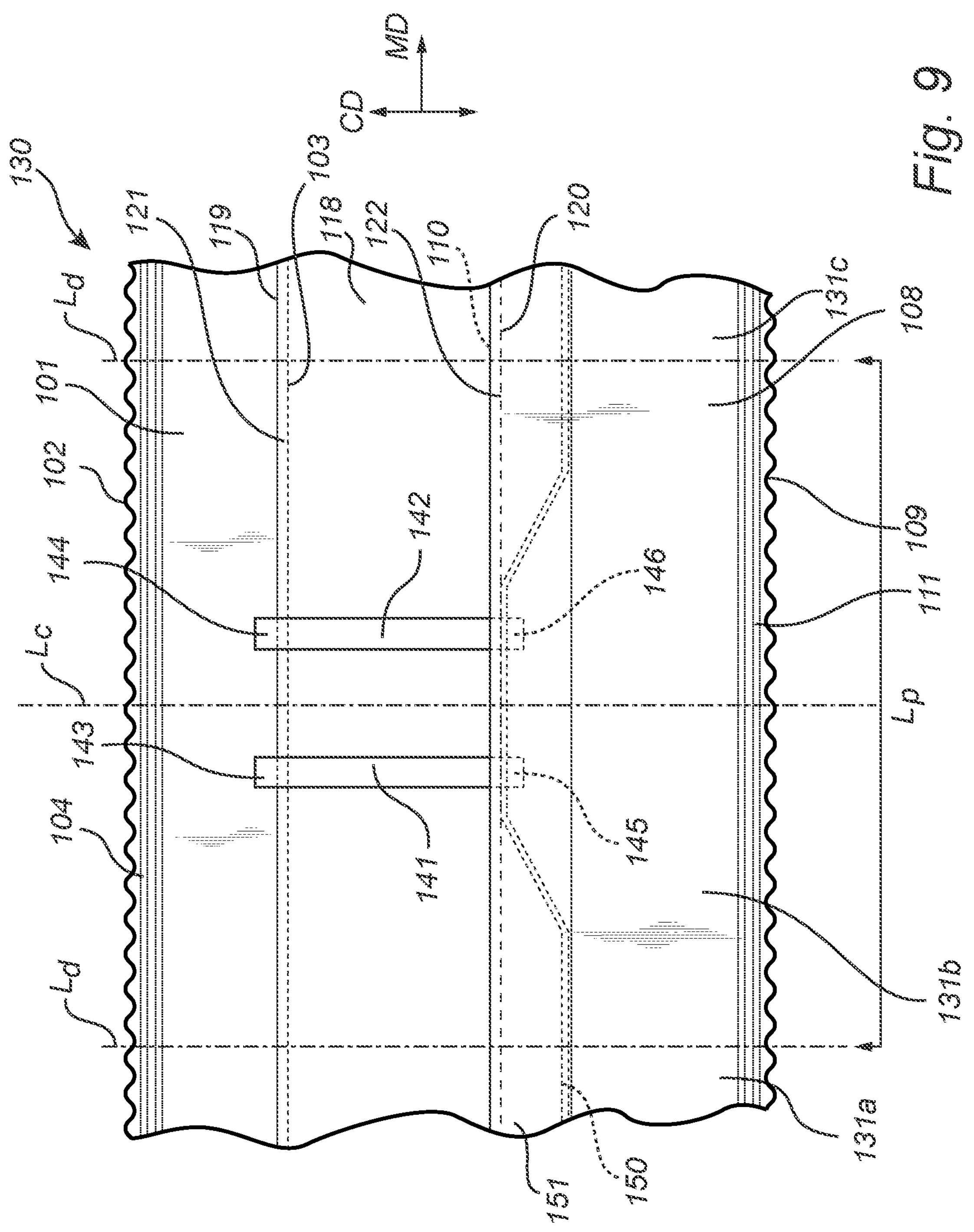

With reference to FIG. 9, a continuous reinforcing leg elastic member 150 is stretched in the machine direction MD and is attached in a stretched state in a curved configuration along the crotch edge 110 of the tensioned rear panel web 108.

The reinforcing leg elastic member 150 is attached in an attachment area or multiple attachment areas (not shown) created on the tensioned rear panel web 108 by continuously or discontinuously applying adhesive to selected portions of the tensioned rear panel web 108 prior to application of the reinforcing leg elastic member 150. After attachment of the reinforcing leg elastic member 150 the leg elastic member 150 and any exposed adhesive may be covered with a nonwoven covering web 151, as shown in FIG. 9.

The reinforcing leg elastic member 150 extends over and is attached to the preferably non-tensioned second end portions 145, 146 of the first and second crotch elastic members 141, 142.

Figure 10:
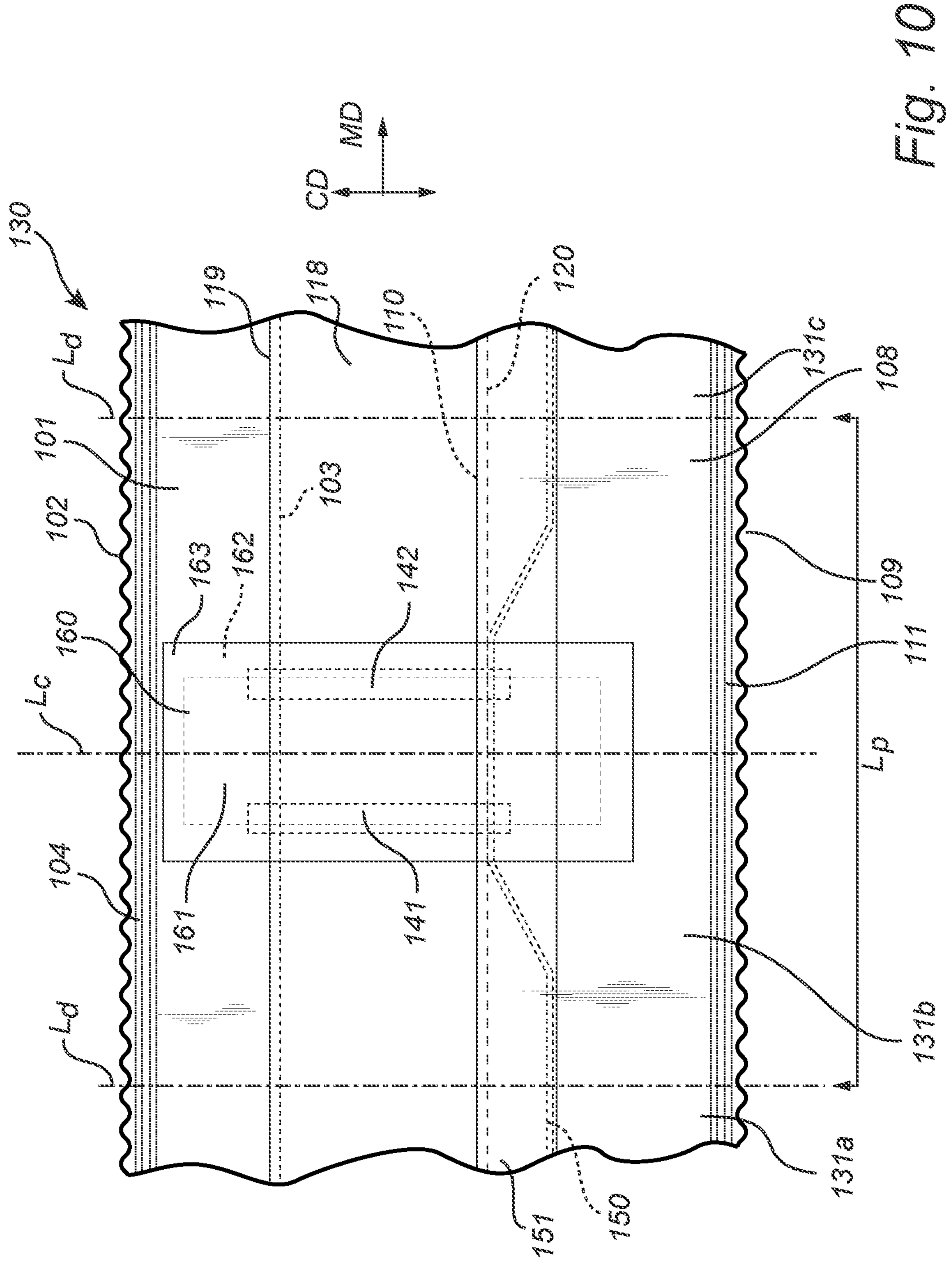

As illustrated in FIG. 10, the method may further comprise applying and attaching an absorbent assembly 160 comprising an absorbent core 161 to the moving chassis web 130. The absorbent assembly 161 further comprises a liquid impermeable backsheet 162 and a liquid permeable topsheet 163 which together enclose the absorbent core 161.

The absorbent assembly 160 is applied on the precursor article centerline Lc and covers the stretched and attached crotch elastic members 141, 142.

The absorbent core 161 is disposed between the topsheet 163 and the backsheet 162 to absorb liquid, such as urine or other bodily fluids, which has passed through the topsheet 163.

The topsheet 163, backsheet 162 and the absorbent core 161 may consist of any materials suitable for their purposes.

The absorbent core 161 may be a single-layer structure or may be a layered structure. The absorbent core 161 may comprise suitable amounts of superabsorbent material. Such superabsorbent material is well known in the field of absorbent articles and is constituted by water-swellable and water-insoluble material which is capable of absorbing large quantities of fluid upon formation of a hydrogel. The absorbent core 161 may contain superabsorbent material in the form of fibers or particles of absorbent polymer material. For example, the superabsorbent material may be surface cross-linked, partially neutralized polyacrylates. The superabsorbent material e.g., the superabsorbent fibers or particles, may be mixed with other absorbent or liquid uptake material or materials, such as cellulose fluff pulp, and/or be arranged in pockets or layers in the absorbent core 161.

The absorbent core 161 may further comprise components for improving properties of the absorbent core 161, such as integrity and strength. For example, the absorbent core 161 may comprise a binder or binders, such as binder fibers. Resilient fibers, chemically stiffened fibers, etc. may be present in the absorbent core 161 to counteract wet-collapse of cellulosic fibers. Such fibers may also be useful in retaining a fluid transporting capillary network in the absorbent component so that absorbent fluid may be distributed in the absorbent component and be absorbed by superabsorbent material also in parts of the absorbent component outside the initial wetting area of the absorbent article.

The topsheet 163 is a wearer-facing layer and may comprise or consist of a fluid permeable nonwoven fabric, a perforated polymer film, mesh or foam. The topsheet may be made from thermoplastic material, such as thermoplastic synthetic fibers, film or netting. The topsheet 163 may consist of a single layer or may have a laminate structure comprising a plurality of layers, for example, two or more layers. The layers may be made of the same material, or some or all layers may be made of different materials.

Furthermore, the backsheet 162 may be constituted by a liquid-impermeable layer such as a polymeric film, for example a film of polyethylene or polypropylene. The backsheet 162 may be breathable. The materials which may be used for the backsheet 162 include thin and flexible fluid impermeable plastic films, or fluid impermeable nonwoven materials, fluid impermeable foams and fluid impermeable laminates. The backsheet 162 may be formed by a single layer, or may be a multi-layered structure, with at least one layer being fluid impermeable.

After the optional application and attachment of an absorbent assembly 160 to the chassis web 130, leg cuts 170 are formed in the chassis web 130 between the precursor articles 131*a*, 131*b*, 131*c*, each leg cut 170 having a closed loop configuration as indicated between the precursor articles 131*b* and 131*c* in FIG. 6. The leg cuts form a first leg edge 171 of the leading precursor article 131*c* and a second leg edge of the trailing precursor article 131*b;*

Figure 11:
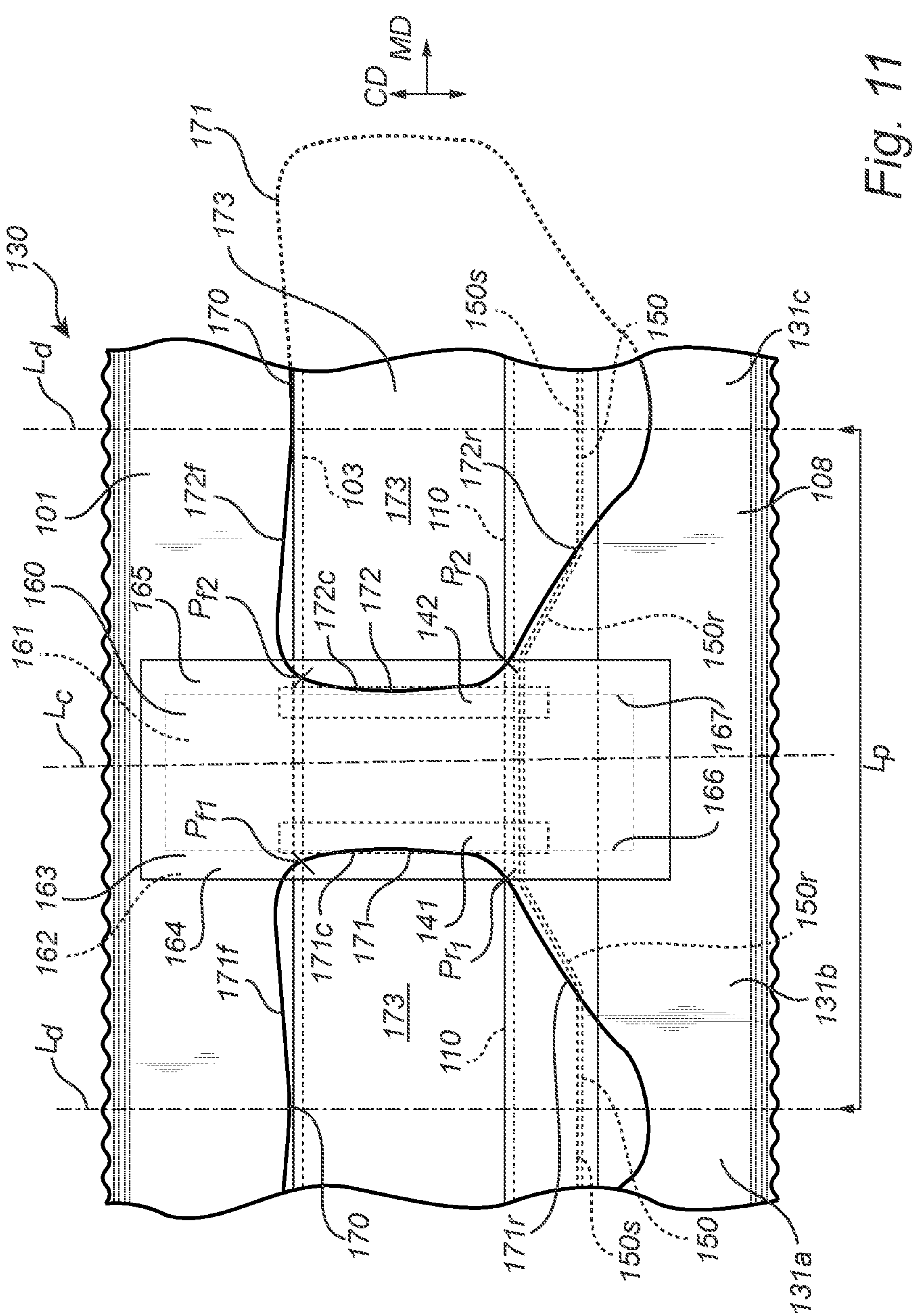

As shown in FIG. 11, the first leg edge 171 of each precursor article 131*a*, 131*b*, 131*c* in the chassis web 130 consists of:

- a front leg edge section 171*f* extending in the tensioned front panel web 101;
- a crotch leg edge section 171*c* extending in the crotch panel web 118 between the front panel crotch edge 103 and the rear panel crotch edge 110; and
- a rear leg edge section 171*r* extending in the tensioned rear panel web 108.

The second leg edge 172 of each precursor article 131*a*, 131*b*, 131*c*, consists of:

- a front leg edge section 172*f* extending in the tensioned front panel web 101;
- a crotch leg edge section 172*c* extending in the crotch panel web 118 between the front panel crotch edge 103 and the rear panel crotch edge 110; and
- a rear leg edge section 172*r* extending in the tensioned rear panel web 108.

As shown in FIG. 11, the closed-loop leg cuts 170 form cut-out portions 173 having an approximate heart-shape inside each leg cut 170. The shape of the leg cuts 170 and the outline of the cut-out portions are described in more detail with reference to the pant-type article 1 which is shown in FIGS. 1A, 1B, 1C and FIGS. 3-5. The outline of the cut-out portions 173 correspond to the outline of the combined leg edges 11, 12 which is shown in FIG. 2.

After forming the leg cuts 170, the cut-out portions 173 are removed from the chassis web and are not further part of the process as disclosed herein.

The length of each of the crotch leg edge sections 171*c*, 172*c*, is measured along the corresponding leg edge 171, 172 from a forward point Pf1, Pf2 on the leg edge 171, 172 where the leg edge 171, 172 intersects with the front panel crotch edge 103 to a rearward point Pr1, Pr2 on the leg edge 171, 172 where the leg edge 171, 172 intersects with the rear panel crotch edge 110.

The length of the front leg edge section 171*f* of the first leg edge 171 is measured along the first leg edge 171 from the forward point Pf1 on the first leg edge 171 where the first leg edge 171 intersects with the front panel crotch edge 103, to the dividing line Ld which is behind the first leg edge 171 in the machine direction MD that is, to the dividing line Ld which is closest to the forward point Pf1.

The length of the rear leg edge section 171*r* of the first leg edge 171 is measured along the first leg edge 171 from the rearward point Pr1 on the first leg edge 171 where the first leg edge 171 intersects with the rear panel crotch edge 108, to the dividing line Ld which is behind the first leg edge 171 in the machine direction MD that is, to the dividing line Ld which is closest to the rearward point Pr1.

The length of the front leg edge section 172*f* of the second leg edge 172 is measured along the second leg edge 172 from the forward point Pf2 on the second leg edge where the second leg edge 172 intersects with the front panel crotch edge 103, to the dividing line Ld which is in front of the second leg edge 172, in the machine direction MD that is, to the dividing line Ld which is closest to the forward point Pf2.

The length of the rear leg edge section 172*r* of the second leg edge 172 is measured along the second leg edge 172 from the rearward point Pr2 on the second leg edge 172 where the second leg edge 172 intersects with the rear panel crotch edge 108 to the dividing line Ld which is in front of the second leg edge 172 in the machine direction MD that is, to the dividing line Ld which is closest to the rearward point Pr2.

Figure 12:
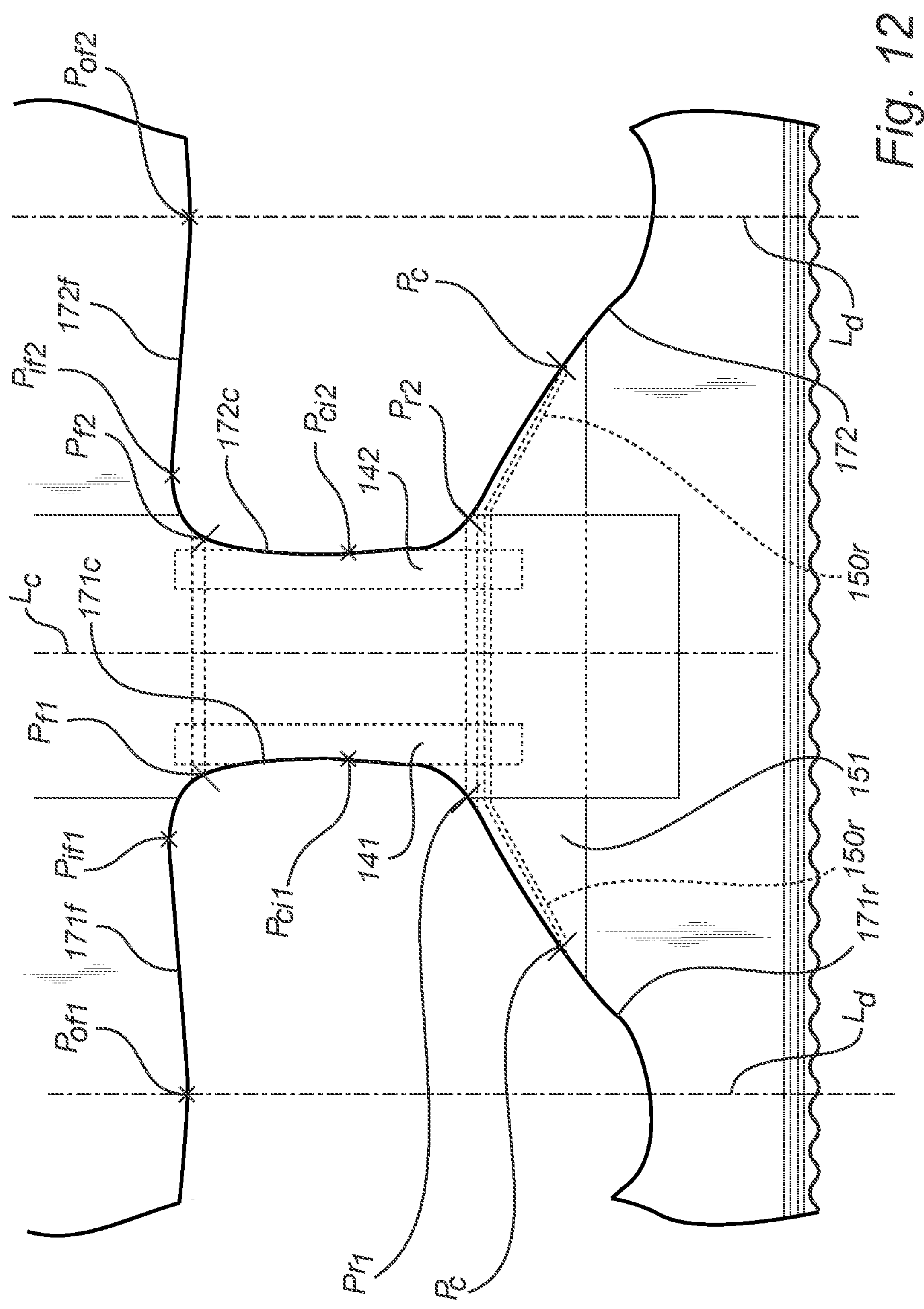
FIG. 12 shows a detail of FIG. 11.

As seen in FIG. 12, each front leg edge section 171*f*, 172*f* has an inner point Pif1, Pif2 located proximal to the crotch leg edge section 171*c*, 172*c* of the leg edge 171, 172 which inner point Pif1, Pif2 is closer to the front waist edge 102 than an outer point Pof1, Pof2 on the front leg edge section 171*f*, 172*f*, which outer point Pof1, Poif2 is distal from the crotch leg edge section 171*c*, 172*c*. The outer point Pof1, Pof2 is located at the corresponding dividing line Ld between the precursor articles 131*a*, 131*b*, 131*c*.

With further reference to FIG. 12, each crotch leg edge section 171*c*, 172*c* has an intermediate point Pci1, Pci2 located between the front crotch edge 103 and the rear crotch edge 110, where the distance between the first leg edge 171 and the second leg edge 172 is smaller than at the forward point Pf1, Pf2 of the crotch leg edge section 171*c*, 172*c* where the leg edge 171, 172 intersects with the front crotch edge 103, After forming the leg cuts, the absorbent assemblies 160 will be located centrally between the first leg edge 171 and the second leg edge of each precursor article 131*a*, 131*b*, 131*c* in the chassis web.

As shown in FIG. 11, a part of each crotch leg edge section 171*c*, 172*c* is formed by cutting through the crotch panel web 118, through the corresponding crotch elastic member 141, 142 and through a peripheral edge portion 164, 165 of the absorbent assembly 160. The peripheral edge portions 164, 165 of the absorbent assembly 160 are formed by portions of the liquid impermeable backsheet 162 and the liquid permeable topsheet 163 of the absorbent assembly 160 which extend in the machine direction MD outward of a corresponding peripheral edge 166, 167 of the absorbent core 161 of the absorbent assembly 160. In the absorbent assembly 160 shown in the Figures, the topsheet 163 and the backsheet 162 both extend beyond the peripheral edges 166, 167 of the absorbent core 161 and are joined to each other in an edge seal.

The crotch leg edge sections 171*c*, 172*c* are cut with a slightly concave curvature, as seen in FIG. 6 such that also the band-shaped crotch elastic members 141, 142 which initially have a generally rectangular shape are given a somewhat modified band-shape with a concave cut edge along at least part of the crotch leg edge sections 171*c*, 172*c*.

With further reference to FIG. 11 and to FIG. 12, when cutting the rear leg edge sections 171*r*, 172*r* of the first and second leg edges 171, 172 surplus parts 150*s* of the reinforcing elastic element 150 are simultaneously cut away together with the cut-out portion 173, leaving a remaining part 150*r* of the reinforcing elastic element 150 being attached along the rear leg edge section 171*r*, 172*r* of each of the first leg edge 171 and the second leg edge 172 between the rearward point Pr1, Pr2 of each leg edge 171, 172 where the leg edge 171, 172 intersects with the rear panel crotch edge 110 and the cutting point Pc on the leg edge where the reinforcing elastic element 150 is cut off. Thereby, a portion of each rear leg edge section 171*r*, 172*r* between the cutting point Pc and the dividing line Ld which is closest to the cutting point Pc, is free from reinforcing elastic. The portion of each rear leg edge section 171*r*, 172*r* which is free from the reinforcing elastic element 150 may have a length as measured along the corresponding leg edge 171, 172 from the cutting point Pc to the closest dividing line Ld which is from 25% to 75% of the total length of the rear leg edge section 171*r*, 172*r*.

Figure 13:
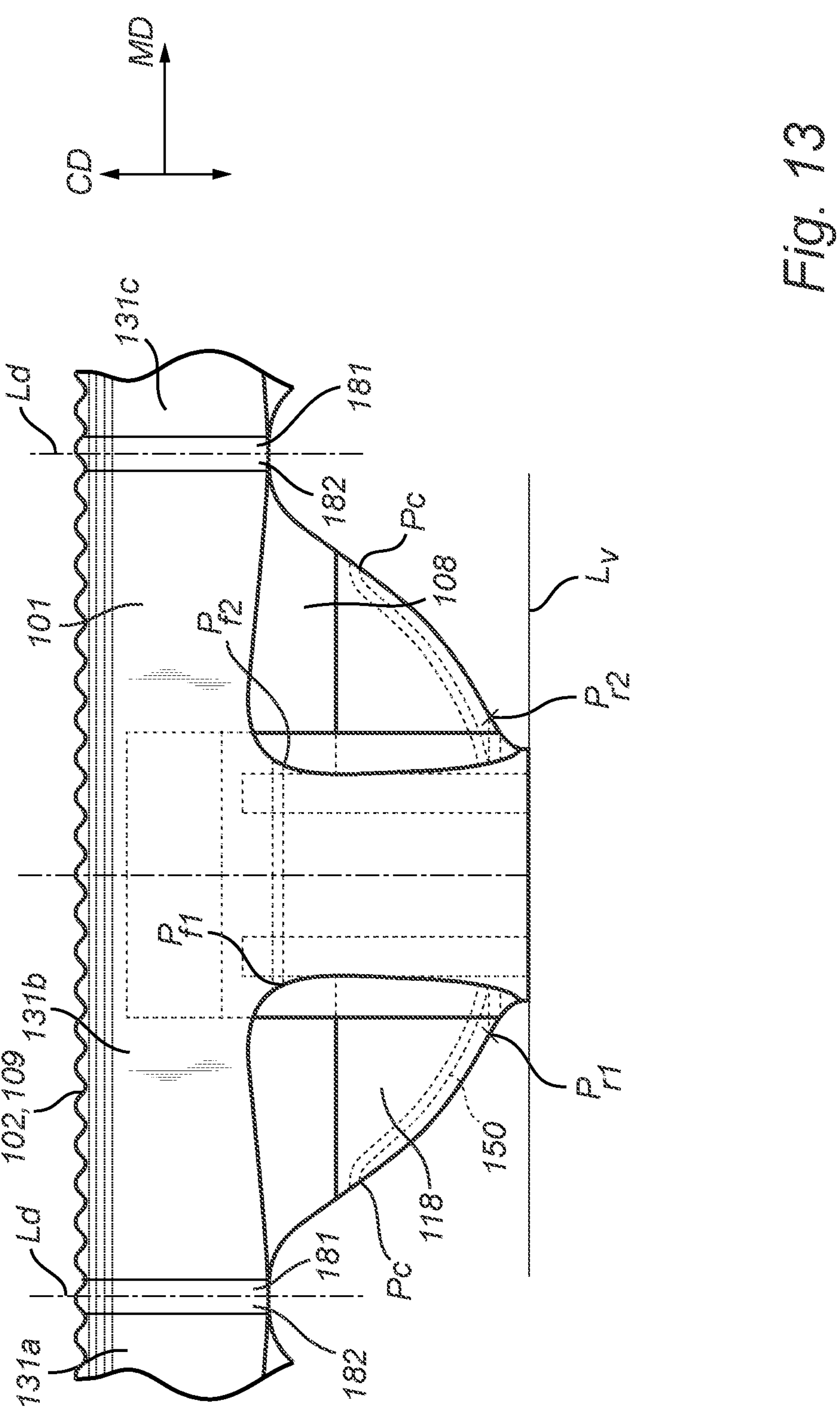
FIG. 13 shows a planar view of a section of the chassis web in FIGS. 6-11 in a final stage of production.

After forming the leg edges 171, 172 by cutting out the cut-out portion 173 from the chassis web 130 along the cutting line 170, the chassis web 130 is folded along a fold-line Lv extending in the machine direction MD to bring the waist edge 102 of the front panel web 101 into alignment with the waist edge 109 of the rear panel web 108 as shown in FIG. 13.

A first side seam 181 and a second side seam 182 are formed in each precursor article 131*a*, 131*b*, 131*c* along the dividing lines Ld between the precursor articles 131*a*, 131*b*, 131*c*, from the aligned waist edges 102, 109 of the front and rear panel webs 101, 108, to the leg cuts 170.

The first side seam 181 of a leading precursor article 131*a* and the second side seam 182 of a trailing precursor article 131*b* may be formed as a single broad seal extending along the dividing line Ld, as shown in FIG. 13. When cutting away individual pant-type articles from the chassis web 130 of precursor articles 131*a*, 131*b*, 131*c* by severing the chassis web along the dividing lines Ld, the single broad seal shown in FIG. 13 will at the same time be divided into the two side seams 181, 182 of the interconnected precursor articles 131*a*, 131*b*.

Alternatively, the side seams 181, 182 may be formed as individual seals placed on each side of the dividing line Ld.

The side seams may be formed by any method suitable for the purpose, such as by thermo-welding, ultrasonic welding or by means of adhesive. In case of adhesive side seals, the adhesive is generally applied before the chassis web is folded along the folding line Lv.

The invention claimed is:

1. A disposable pant-type article, the article having a longitudinal direction and a transverse direction, with a longitudinal centre line extending in the longitudinal direction, the article comprising:

a front body panel being elastically stretchable in the transverse direction, the front body panel having a front waist edge, a front crotch edge opposite the front waist edge and a first and a second longitudinal side edge;

a rear body panel being elastically stretchable in the transverse direction, the rear body panel having a rear waist edge, a rear crotch edge opposite the rear waist edge and a first and a second longitudinal side edge;

a crotch region being located between the front panel crotch edge and the rear panel crotch edge, the crotch region being contiguous with the front body panel along the front panel crotch edge and being contiguous with the rear body panel along the rear panel crotch edge;

wherein the first longitudinal side edge of the front body panel is joined to the first longitudinal side edge of the rear body panel in a first side seam and the second longitudinal side edge of the front body panel is joined to the second longitudinal side edge of the rear body panel in a second side seam, the article having a waist opening and a first and a second leg opening, the first leg opening being bordered by a first leg edge and the second leg opening being bordered by a second leg edge, each of the first and the second leg edges being constituted by a front leg edge section a crotch leg edge section and a rear leg edge section;

the front body panel comprises a front panel web being elastically stretchable in the transverse direction, the front leg edge section of each of the first and the second leg edge being arranged in the elastically stretchable front panel web;

the rear body panel comprising a rear panel web being elastically stretchable in the transverse direction, the rear leg edge section of each of the first and the second leg edge being arranged in the elastically stretchable rear panel web;

the crotch region comprising a crotch region web, the crotch leg edge section of each of the first and the second leg edge being arranged in the crotch region web from the front crotch edge to the rear crotch edge;

wherein each front leg edge section having an inner point being located on the front leg edge section at a greater distance from the corresponding side seam than from the longitudinally extending centre line, an outer point constituting an endpoint of the front leg edge section being located at the corresponding side seam, a distance between the inner point of the front leg edge section and the front waist edge being the smallest distance between the front leg edge section and the front waist edge and being smaller than a distance between the outer point of the front leg edge section and the front waist edge;

and each crotch leg edge section having an intermediate point located between the front crotch edge and the rear crotch edge which intermediate point is closer to the longitudinal centre line than a front endpoint of the crotch leg edge section where the leg edge intersects with the front crotch edge.

2. A disposable pant-type article according to claim 1, wherein the distance between the outer point of each front leg edge section and the front waist edge constitutes the greatest distance between the front leg edge section and the front waist edge in a part of the front leg edge section which is defined between the inner point of the front leg edge section and the side seam.

3. A disposable pant-type article according to claim 1, wherein a distance between each inner point on each front leg edge section and the longitudinally extending centre line is 30 to 50% of a distance between the longitudinally extending centre line and the corresponding side seam, the distances being measured in the transverse direction, perpendicular to the longitudinally extending centre line.

4. A disposable pant-type article according to claim 1, wherein the inner point on each front leg edge section is arranged closer to the front waist edge than the outer point by at least 5 millimetres and by at most 40 millimetres.

5. A disposable pant-type article according to claim 4, wherein the inner point on each front leg edge section is arranged closer to the front waist edge than the outer point by at most 20 millimeters.

6. A disposable pant-type article according to claim 1, wherein the intermediate point on each crotch leg edge section is closer to the longitudinal centre line than a rear end point of the crotch leg edge section where the leg edge intersects with the rear crotch edge.

7. A disposable pant-type article according to claim 1, wherein the distance between the intermediate point on each crotch leg edge section and the longitudinal centre line is smaller than the distance between the front endpoint and the longitudinal centre line by from 2 millimetres to 30 millimetres.

8. A disposable pant-type article according to claim 6, wherein the distance between the intermediate point on each crotch leg edge section and the longitudinal centre line is smaller than the distance between the rear endpoint and the longitudinal centre line by from 5 millimetres to 60 millimetres.

9. A disposable pant-type article according to claim 1, wherein each rear leg edge section has a buttocks portion with a convex curvature.

10. A disposable pant-type article according to claim 9, wherein each rear leg edge section has a transition point where the convex curvature of the buttocks portion of the rear leg edge section changes into a linear hip portion or into a hip portion having a concave curvature, the transition point being located at a distance of from 30 millimetres to 100 millimetres from the corresponding side seam.

11. A disposable pant-type article according to claim 1, wherein the article further comprises an absorbent assembly, the absorbent assembly comprising an absorbent core, a liquid permeable topsheet and a liquid impermeable backsheet, the absorbent core being enclosed between the liquid permeable topsheet and the liquid impermeable backsheet.

12. A disposable pant-type article according to claim 11, wherein the intermediate point on each crotch leg edge section is arranged on a side edge of the absorbent assembly.

13. A disposable pant-type article according to claim 1, wherein a pre-tensioned first crotch elastic member is arranged extending in the longitudinal direction along the first leg edge between the front crotch edge and the rear crotch edge and a pre-tensioned second crotch elastic member is arranged extending in the longitudinal direction along the second leg edge between the front crotch edge and the rear crotch edge.

14. A disposable pant-type article according to claim 13, wherein the intermediate point on each crotch leg edge section is arranged on a side edge of the corresponding crotch elastic member.

15. A disposable pant-type article according to claim 14, wherein each crotch elastic member has a smallest width at the intermediate point on the crotch leg edge section.

16. A disposable pant-type article according to claim 13, wherein a front end portion of each of the first and the second crotch elastic member overlaps with and is attached to the front body panel and/or a rear end portion of each of the first and the second crotch elastic member overlaps with and is attached to the rear body panel.

17. A disposable pant-type article according to claim 1, wherein a first reinforcing elastic feature is arranged on the elastically stretchable rear body panel along at least a first part of the rear leg edge section of the first leg edge and a second reinforcing elastic feature is arranged on the elastically stretchable rear body panel along at least a first part of the rear leg edge section of the second leg edge.

18. A disposable pant-type article according to claim 1, wherein the crotch region web is a non-stretchable material.

19. A disposable pant-type article according to claim 1, wherein the elastically stretchable front panel web and/or the elastically stretchable rear panel web comprises or consists of an elastic laminate, the elastic laminate comprising at least a first layer of non-stretchable fibrous material and an elastic layer.

20. A disposable pant-type article according to claim 19, wherein the elastic laminate comprises a second layer of fibrous material and the elastic layer is an intermediate elastic layer arranged between the first and second layers of fibrous material.

21. A disposable pant-type article according to claim 19, wherein the elastic layer comprises or consists of a layer of elastic film.

22. A disposable pant-type article according to claim 19, wherein the elastic layer comprises or consists of a layer of elastic nonwoven material.

* * * * *